United States Patent
Utkhede et al.

(10) Patent No.: US 11,957,784 B2
(45) Date of Patent: *Apr. 16, 2024

(54) OPHTHALMIC DRUG SUSTAINED RELEASE FORMULATION AND USES THEREOF

(71) Applicant: Mati Therapeutics, Inc.

(72) Inventors: Deepank Utkhede, Surrey (CA); Catherine Jones, Burnaby (CA); David J. Wiseman, Surrey (CA)

(*) Notice: Subject to any disclaimer, the term of this patent is extended or adjusted under 35 U.S.C. 154(b) by 0 days.

This patent is subject to a terminal disclaimer.

(21) Appl. No.: 17/740,192

(22) Filed: May 9, 2022

(65) Prior Publication Data

US 2023/0091568 A1 Mar. 23, 2023

Related U.S. Application Data

(63) Continuation of application No. 16/833,883, filed on Mar. 30, 2020, now Pat. No. 11,324,693, which is a continuation of application No. 15/722,227, filed on Oct. 2, 2017, now Pat. No. 10,603,274, which is a continuation of application No. PCT/US2017/054654, filed on Sep. 30, 2017.

(60) Provisional application No. 62/402,938, filed on Sep. 30, 2016.

(51) Int. Cl.
| | | |
|---|---|---|
| *A61F 9/00* | (2006.01) | |
| *A61F 9/007* | (2006.01) | |
| *A61K 9/00* | (2006.01) | |
| *A61K 9/14* | (2006.01) | |
| *A61K 31/165* | (2006.01) | |
| *A61K 31/569* | (2006.01) | |
| *A61K 31/573* | (2006.01) | |
| *A61K 38/13* | (2006.01) | |
| *A61K 47/10* | (2017.01) | |
| *A61K 47/34* | (2017.01) | |

(52) U.S. Cl.
CPC .......... *A61K 9/0051* (2013.01); *A61F 9/0017* (2013.01); *A61F 9/00772* (2013.01); *A61K 9/146* (2013.01); *A61K 31/165* (2013.01); *A61K 31/569* (2013.01); *A61K 31/573* (2013.01); *A61K 38/13* (2013.01); *A61K 47/10* (2013.01); *A61K 47/34* (2013.01)

(58) Field of Classification Search
CPC .... A61K 9/0051; A61K 9/146; A61K 31/165; A61K 31/569; A61K 31/573; A61K 38/13; A61K 47/10; A61K 47/34; A61F 9/0017; A61F 9/00772
See application file for complete search history.

(56) References Cited

U.S. PATENT DOCUMENTS

| | | | |
|---|---|---|---|
| 5,273,530 | A | 12/1993 | Cerro et al. |
| 5,409,457 | A | 4/1995 | Cerro et al. |
| 5,632,773 | A | 5/1997 | Graham et al. |
| 10,603,274 | B2 * | 3/2020 | Utkhede et al. |
| 10,825,047 | B2 | 11/2020 | Vorozhtsov |
| 11,324,693 | B2 * | 5/2022 | Utkhede et al. |
| 11,571,147 | B2 | 2/2023 | Hayter et al. |
| 11,695,537 | B2 | 7/2023 | Terwal |
| 11,695,545 | B2 | 7/2023 | Menon et al. |
| 2002/0002362 | A1 | 1/2002 | Humayun et al. |
| 2004/0170685 | A1 | 9/2004 | Carpenter et al. |
| 2005/0048121 | A1 | 3/2005 | East et al. |
| 2005/0055701 | A1 | 3/2005 | Stall |
| 2005/0129731 | A1 | 6/2005 | Horres et al. |
| 2005/0244464 | A1 | 11/2005 | Hughes |
| 2006/0009498 | A1 | 1/2006 | Whitcup |
| 2006/0233860 | A1 | 10/2006 | Chang et al. |
| 2007/0280992 | A1 | 12/2007 | Margaron et al. |
| 2008/0107694 | A1 | 5/2008 | Trogden et al. |
| 2008/0113027 | A1 * | 5/2008 | Asgharian et al. |
| 2008/0145403 | A1 | 6/2008 | Spada et al. |
| 2008/0231986 | A1 | 9/2008 | Aoki et al. |
| 2008/0231987 | A1 | 9/2008 | Bierhoff |
| 2008/0231989 | A1 | 9/2008 | Oki et al. |
| 2008/0283002 | A1 | 11/2008 | Mantheakis et al. |
| 2008/0292679 | A1 | 11/2008 | Lyons et al. |
| 2009/0196905 | A1 | 8/2009 | Spada et al. |
| 2010/0209477 | A1 | 8/2010 | Butuner et al. |
| 2011/0054031 | A1 | 3/2011 | McNamara et al. |
| 2011/0182966 | A1 | 7/2011 | Robinson et al. |
| 2015/0105468 | A1 | 4/2015 | Martinez-Alzamora et al. |
| 2015/0133546 | A1 | 5/2015 | Butuner et al. |

* cited by examiner

*Primary Examiner* — Alma Pipic
(74) *Attorney, Agent, or Firm* — Koren Anderson

(57) ABSTRACT

A solid matrix sustained release ophthalmic formulation for topical delivery of a solid ophthalmic drug to the eye, medical devices, drug cores, drug inserts and drug delivery systems comprising the formulation, methods of manufacturing the formulation, medical devices and their methods thereof for delivering the ophthalmic drug for a treatment period provided herein. The formulation disclosed herein is an admixture of an ophthalmic drug, and a combination of a hydrophobic polymer, a hydrophilic polymer and a surfactant, wherein the drug is eluted daily over an extended period of time at therapeutic dose of drug.

20 Claims, 18 Drawing Sheets

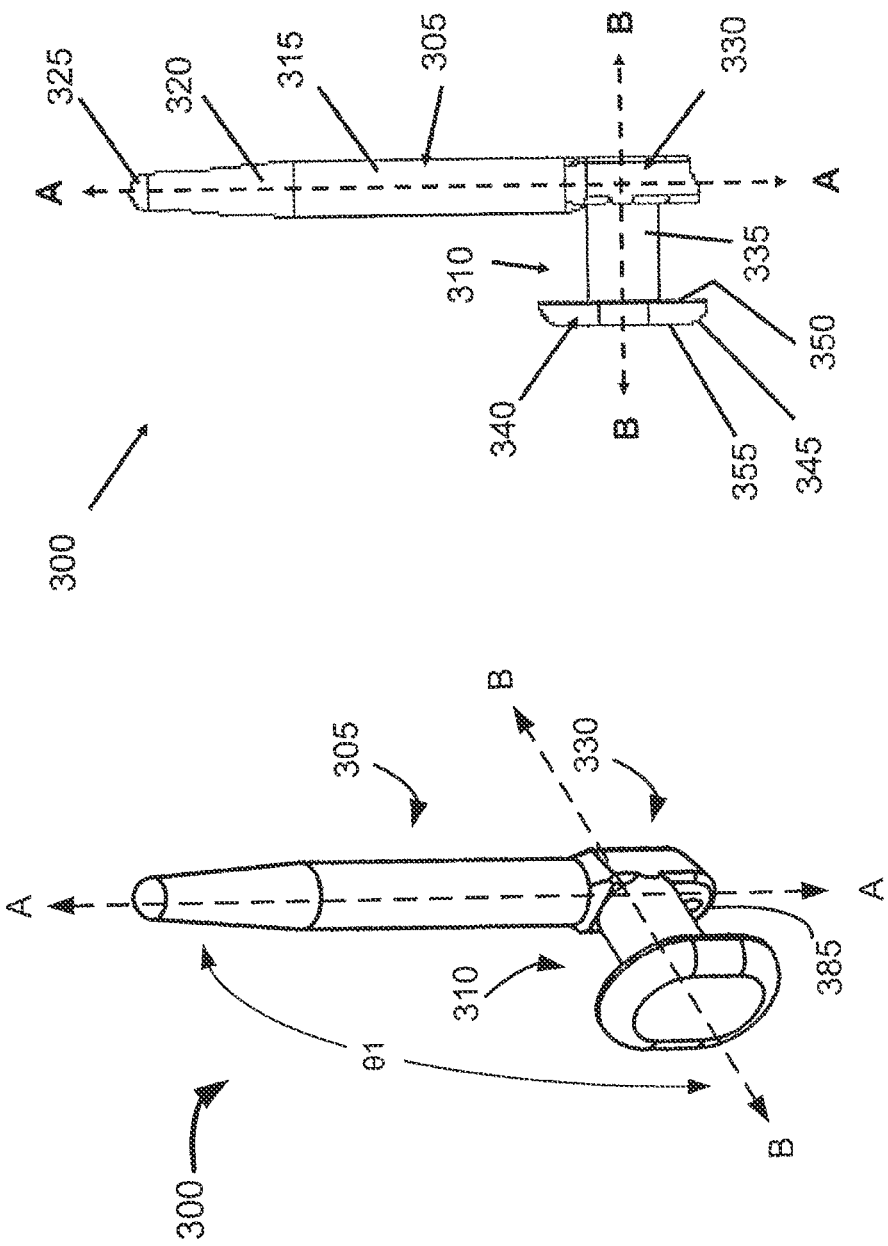

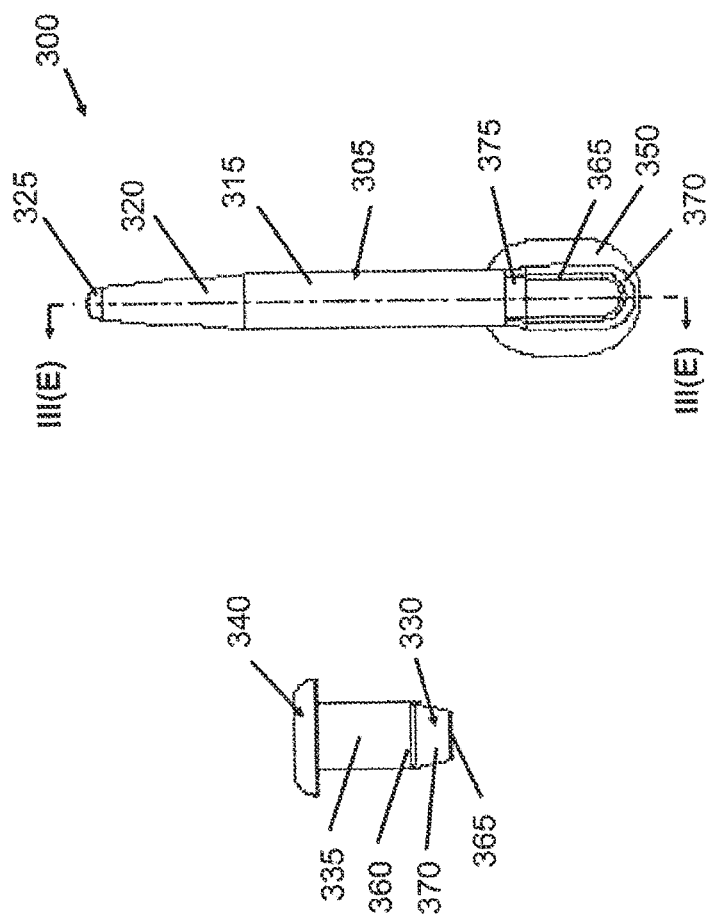

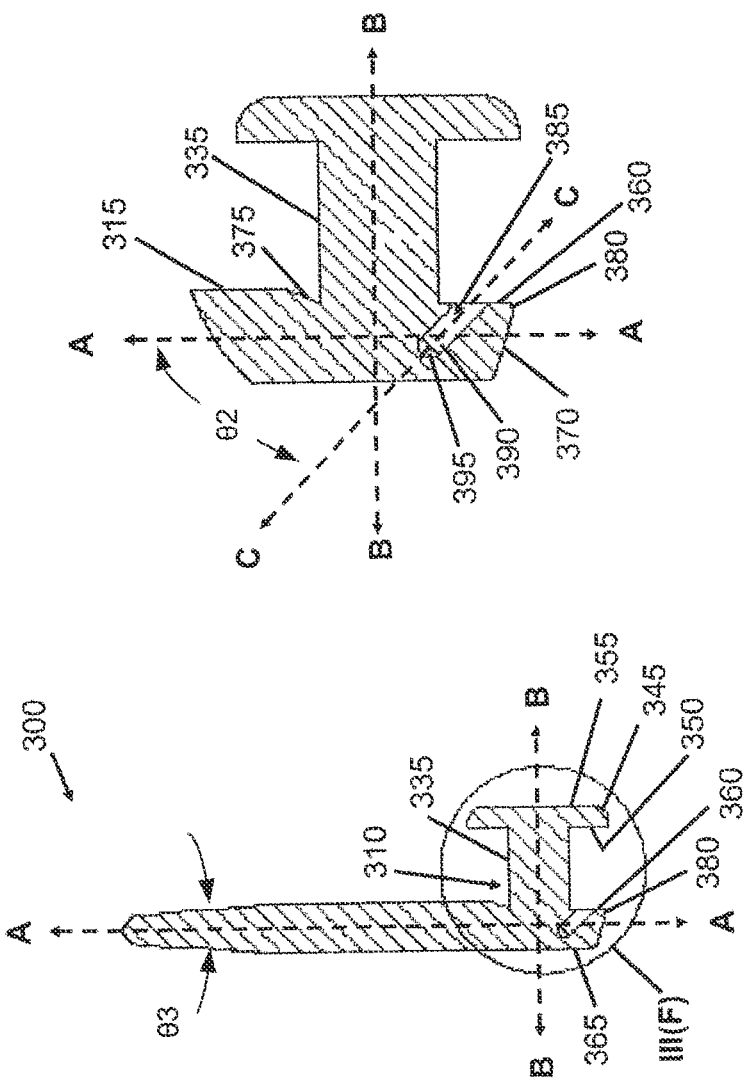

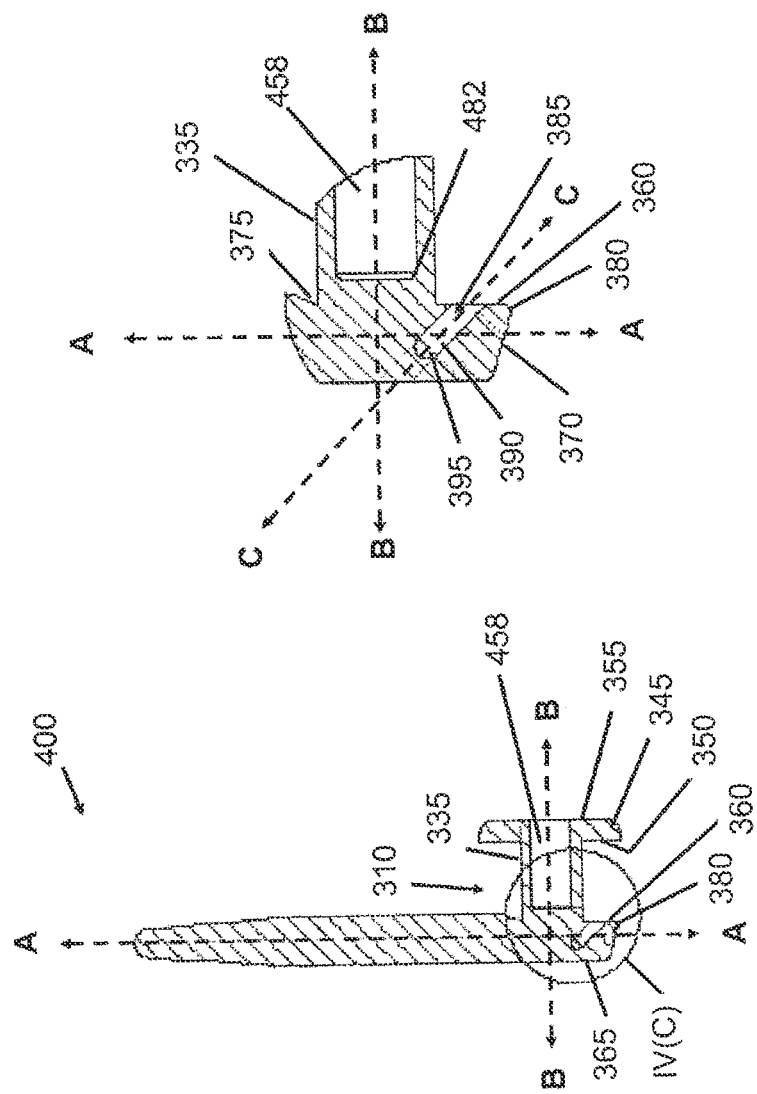

OPHTHALMIC DRUG SUSTAINED RELEASE FORMULATION AND USES THEREOF

CROSS-REFERENCE TO RELATED APPLICATIONS

This application is a continuation application of U.S. Ser. No. 16/833,883, filed 30 Mar. 2020, which is a continuation application of U.S. Ser. No. 15/722,227, filed 2 Oct. 2017, which is a continuation application of PCT/US17/54654, filed 30 Sep. 2017 and which claims the benefit of U.S. Provisional Patent Application No. 62/402,938, filed on 30 Sep. 2016, the contents of which are each incorporated herein by reference in their entirety.

FIELD OF THE INVENTION

This application pertains generally to solid matrix sustained release formulations for topical delivery of ophthalmic drugs to the eye and their uses thereof for methods of treating ocular diseases.

BACKGROUND OF THE INVENTION

Lacrimal implants are devices that are inserted into a punctum and an associated lacrimal canaliculus of an eye, either to block drainage of tears (to prevent conditions such as dry eye), or to contain a quantity of drug for release into the eye.

FIGS. 1-2 illustrate example views of anatomical tissue structures associated with an eye 100. Certain of the anatomical tissue structures shown may be suitable for treatment using the various lacrimal implants and methods discussed herein. The eye 100 is a spherical structure including a wall having three layers: an outer sclera 102, a middle choroid layer 104 and an inner retina 106. The sclera 102 includes a tough fibrous coating that protects the inner layers. It is mostly white except for the transparent area at the front, commonly known as the cornea 108, which allows light to enter the eye 100.

The choroid layer 104, situated inside the sclera 102, contains many blood vessels and is modified at the front of the eye 100 as a pigmented iris 110. A biconvex lens 112 is situated just behind the pupil. A chamber 114 behind the lens 112 is filled with vitreous humor, a gelatinous substance. Anterior and posterior chambers 116 are situated between the cornea 108 and iris 110, respectively and filled with aqueous humor. At the back of the eye 100 is the light-detecting retina 106.

The cornea 108 is an optically transparent tissue that conveys images to the back of the eye 100. It includes a vascular tissue to which nutrients and oxygen are supplied via bathing with lacrimal fluid and aqueous humor as well as from blood vessels that line the junction between the cornea 108 and sclera 102. The cornea 108 includes a pathway for the permeation of drugs into the eye 100.

Turing to FIG. 2, other anatomical tissue structures associated with the eye 100 including the lacrimal drainage system, which includes a secretory system 230, a distributive system and an excretory system, are shown. The secretory system 230 comprises secretors that are stimulated by blinking and temperature change due to tear evaporation and reflex secretors that have an efferent parasympathetic nerve supply and secrete tears in response to physical or emotional stimulation. The distributive system includes the eyelids 202 and the tear meniscus around the lid edges of an open eye, which spread tears over the ocular surface by blinking, thus reducing dry areas from developing.

The excretory system of the lacrimal drainage system includes, in order of flow, drainage, the lacrimal puncta, the lacrimal canaliculi, the lacrimal sac 204 and the lacrimal duct 206. From the lacrimal duct 206, tears and other flowable materials drain into a passage of the nasolacrimal system. The lacrimal canaliculi include an upper (superior) lacrimal canaliculus 208 and a lower (inferior) lacrimal canaliculus 210, which respectively terminate in an upper 212 and lower 214 lacrimal punctum. The upper 212 and lower 214 punctum are slightly elevated at the medial end of a lid margin at the junction 216 of the ciliary and lacrimal portions near a conjunctival sac 218. The upper 212 and lower 214 punctum are generally round or slightly ovoid openings surrounded by a connective ring of tissue. Each of puncta 212, 214 leads into a vertical portion 220, 222 of their respective canaliculus before turning more horizontal at a canaliculus curvature 250 to join one another at the entrance of the lacrimal sac 204. The canaliculi 208, 210 are generally tubular in shape and lined by stratified squamous epithelium surrounded by elastic tissue, which permits them to be dilated. As shown, a lacrimal canaliculus ampulla 252 exists near an outer edge of each canaliculus curvature 250.

A variety of challenges face patients and physicians in the area of drug delivery, for example, ocular drug delivery. In particular, the repetitive nature of the therapies (multiple injections, instilling multiple eye drop regimens per day), the associated costs, and the lack of patient compliance may significantly impact the efficacy of the therapies available, leading to reduction in vision and many times blindness.

Patient compliance in taking the medications, for example, instilling the eye drops, can be erratic, and in some cases, patients may not follow the directed treatment regime. Lack of compliance can include, failure to instill the drops, ineffective technique (instilling less than required), excessive use of the drops (leading to systemic side effects), and use of non-prescribed drops or failure to follow the treatment regime requiring multiple types of drops. Many of the medications may require the patient to instill them up to 4 times a day.

A conventional method of drug delivery is by topical drop application to the eye's surface. Topical eye drops, though effective, can be inefficient. For instance, when an eye drop is instilled in an eye, it often overfills the conjunctival sac (i.e., the pocket between the eye and the associated lids) causing a substantial portion of the drop to be lost due to overflow of the lid margin and spillage onto the cheek. In addition, a large portion of the drop remaining on the ocular surface can be washed away into and through a lacrimal canaliculus, thereby diluting the concentration of the drug before it can treat the eye. Further, in some cases, topically applied medications have a peak ocular effect within about two hours, after which additional applications of the medications should be performed to maintain the therapeutic benefit.

To compound ocular management difficulty, subjects often do not use their eye drops as prescribed. Noncompliance rates by drop users of 25% and greater have been previously reported. This poor compliance can be due to, for example, forgetfulness or an initial stinging or burning sensation caused by the eye drop and experience by a subject. Instilling eye drops in one's own eye can be difficult, in part because of the normal reflex to protect the eye. Therefore, one or more drops may miss the eye. Older subjects may have additional problems instilling drops due to arthritis, unsteadiness, and decreased vision. Pediatric and psychiatric populations pose difficulties as well.

One promising approach to ocular drug delivery is to place an implant that releases a drug in tissue in or near the eye. However, providing a sustained release of a particular ophthalmic drug at a therapeutic dose over a desired period of time is challenging. Moreover, use of a lacrimal implant provides a limited volume which to include the drug and a sustained release matrix, wherein elution of the drug must be both relatively constant and at a therapeutic dose over the desired time period.

In light of the above, it would be desirable to provide sustained release of certain ophthalmic drugs that overcome the at least of the above mentioned shortcomings.

SUMMARY OF THE INVENTION

Herein are provided sustained release formulations for the topical delivery of ophthalmic drugs to the eye, drug inserts and drug delivery systems comprising the formulation, methods of manufacturing the formulation, drug inserts and their methods thereof for delivering the ophthalmic drug for at least two weeks to the eye. In embodiments provided herein is a solid matrix sustained release ophthalmic formulation for topical delivery of an ophthalmic drug to an eye for an extended period of time, comprising at least one hydrophobic polymer and at least one hydrophilic polymer, wherein the hydrophilic polymer is liquid between 20 and 25° C. and the hydrophobic polymer is present at a higher percentage (% w/w) than the hydrophilic polymer; b) a nonionic surfactant; and, c) the ophthalmic drug, wherein the formulation is adapted to release the ophthalmic drug at therapeutically effective levels each day for a period of about two weeks to about 12 weeks. In embodiments, the formulation is configured to elute at least 1 ug of the drug each day. In certain embodiments, the formulation is configured to elute at least 2 ug of the drug each day for a period of at least two weeks.

In embodiments, the hydrophobic polymer is selected from polyester, polycaprolactone, poly(D,L-lactic-co-glycolic acid)(PLGA), poly lactic acid (PLA), polyurethane, poly glycolic acid (PGA) or a combination thereof. In certain embodiments, the hydrophobic polymer comprises polycaprolactone, which may be present in the solid matrix at, or greater than, 15% (w/w), or from about 15 to about 30% (w/w).

In embodiments, the hydrophilic polymer is polyethylene glycol (PEG) polymers, acrylate-derivatized PEG (PEGDA) polymers, polysaccharide polymers, hydrophilic polyanhydrides or a combination thereof. In certain embodiments, the hydrophilic polymer comprises PEG polymers, wherein the PEG polymer may have a molecular weight (Mw) from about 200 to 1000. In embodiments, the PEG polymers comprise PEG 400. In certain embodiments, the PEG polymer is present in the solid matrix at, or less than, 15% (w/w) or from about 5 to about 15% (w/w).

In embodiments, the ophthalmic drug is a non-steroidal anti-inflammatory drug (NSAID) selected from Nepafenac, Bromfenac, salicylate, diclofenac, flurbiprofen, piroxicam, indomethacin, ibuprofen, naproxen, or nabumetone. In alternative embodiments, the ophthalmic drug is a steroidal anti-inflammatory drug selected from corticosteroid, dexamethasone, difluprednate, triamcinolone acetonide, triamcinolone, fluocinolone, cortisone, prednisolone or flumetholone. In certain embodiments, the ophthalmic drug is an anti-glaucoma drug or a drug for treating dry eye. In embodiments, the ophthalmic drug is cyclosporine A.

In embodiments, the NSAID is present from about 60 to about 70% w/w. In certain embodiments, the NSAID is present in the solid matrix from about 50% to 80% (w/w), the hydrophobic polymer is a polycaprolactone polymer which is present from about 15% to about 25% (w/w), the hydrophilic polymer is a PEG polymer which is present from about 5% to about 15% and the nonionic surfactant is present from about 1% to about 15%.

In embodiments, the nonionic surfactant is tyloxapol, a Span (e.g. sorbitan), a BRIJ (surfactant comprising an ethylene, polyethylene or polyoxyethylene moiety), a polysorbate or a combination thereof. In certain embodiments, the surfactant comprises tyloxapol. In certain other embodiments, the surfactant comprises a polysorbate such as polysorbate 80.

In embodiments, the ophthalmic drug is Nepafenac and is present from about 60 to about 70% (w/w), wherein the solid matrix comprises about 30 to about 15% (w/w) of polycaprolactone, about 5 to about 15% (w/w) of PEG 400 and about 1 to about 15% of tyloxapol or polysorbate 80.

In certain embodiments, provided herein is a solid matrix sustained release ophthalmic formulation for topical delivery of a solid ophthalmic drug, comprising: a) at least one hydrophobic polymer and at least one hydrophilic polymer, wherein the hydrophilic polymer are PEG polymers that are liquid between 20 and 25° C. and the hydrophobic polymer is polycaprolactone, wherein the polycaprolactone is present at a higher percentage (% w/w) than the PEG polymer; b) tyloxapol or polysorbate 80; and, c) nepafenac, wherein the formulation is adapted or configured to release the nepafenac at therapeutically effective levels each day for a period of about two weeks to about 12 weeks. In embodiments, the PEG polymer is PEG 400, which may be present in the solid matrix from about 5 to about 15% (w/w). In embodiments, the polycaprolactone is present in the solid matrix from about 15 to about 30% (w/w). In certain other embodiments, the tyloxapol or polysorbate 80 is present in the solid matrix from about 2 to about 8% (w/w) and the nepafenac is present in the solid matrix from about 55 to 75% (w/w).

Accordingly, in embodiments provided herein is a solid matrix sustained release ophthalmic formulation for topical delivery of a solid ophthalmic drug, comprising: a) PEG polymers with a molecular weight (Mw) from about 200 to 1000, wherein the PEG polymers are present in the solid matrix at about 10% (w/w); b) polycaprolactone polymers present at about 20% (w/w); c) tyloxapol or polysorbate 80 present at about 4%; and, c) nepafenac present at about 66% (w/w), wherein the formulation is adapted to release the nepafenac at therapeutically effective levels each day for a period of about two weeks to about 12 weeks.

In other embodiments provided herein is a solid matrix sustained release ophthalmic formulation for topical delivery of a solid ophthalmic drug, comprising: a) at least one hydrophobic polymer and at least one hydrophilic polymer; b) a nonionic surfactant; and, c) the ophthalmic drug, wherein the formulation is adapted to release the ophthalmic drug at therapeutically effective levels each day for a period of about two weeks to about 12 weeks.

In embodiments, the hydrophilic polymer comprises PEG polymers, wherein the PEG polymers have a molecular weight (Mw) of about 1000 to about 20,000. In certain embodiments, the PEG polymers comprise PEG 2000. In embodiments, the PEG polymers are present from about 5 to about 30% (w/w) or from about 15% to about 30% (w/w).

In embodiments, the ophthalmic drug is cyclosporine. In certain embodiments, the ophthalmic drug is cyclosporine and the solid matrix comprises polycaprolactone, PEG 2000 and a polysorbate surfactant. In embodiments, the ophthalmic drug is cyclosporine and is present from about 36 to 60% (w/w) and the solid matrix comprises from about 2.5 to about 40% (w/w) of polycaprolactone, about 5 to about 15% (w/w) of PEG 2000 and about 15 to about 35% (w/w) of polysorbate 80.

In certain embodiments, provided herein is a solid matrix sustained release ophthalmic formulation for topical delivery of a solid ophthalmic drug, comprising: a) at least one hydrophobic polymer and at least one hydrophilic polymer, wherein the hydrophilic polymer is PEG with a molecular weight (Mw) between 1000 and 20,000, and the hydrophobic polymer is polycaprolactone; b) polysorbate; and, c) cyclosporine, wherein the formulation is adapted to release the cyclosporine at therapeutically effective levels each day for a period of about two weeks to about 12 weeks. In embodiments, the PEG polymer is PEG 2000, which may be present in the solid matrix from about 5 to about 15% (w/w). In embodiments, the polycaprolactone is present in the solid matrix from about 2.5 to about 40% (w/w). In embodiments, the polysorbate is polysorbate 80 that may be present in the solid matrix from about 15 to about 35% (w/w). In embodiments, the cyclosporine is present in the solid matrix from about 35 to 65% (w/w).

In embodiments provided herein is a solid matrix sustained release ophthalmic formulation for topical delivery of a solid ophthalmic drug, comprising: a) at least one hydrophilic polymer; b) a nonionic surfactant; and, c) the ophthalmic drug, wherein the formulation is adapted to release the ophthalmic drug at therapeutically effective levels each day for a period of about two weeks to about 12 weeks and wherein the solid matrix does not comprise a hydrophobic polymer. In embodiments, the ophthalmic drug is steroidal anti-inflammatory drug selected from dexamethasone, difluprednate, triamcinolone acetonide, triamcinolone, dexamethasone, fluocinolone, cortisone, prednisolone and flumetholone. In embodiments, the steroidal anti-inflammatory drug is Difluprednate and is present from about 35 to about 55% w/w and the matrix comprises about 40 to about 55% w/w of PEG 2000.

In alternative embodiments, provided herein is a solid matrix sustained release ophthalmic formulation for topical delivery of an ophthalmic drug, comprising: a) a liquid nonionic surfactant; b) a solid nonionic surfactant; and, c) the ophthalmic drug, wherein the formulation is adapted to release the ophthalmic drug at therapeutically effective levels each day for a period of about two weeks to about 12 weeks, and wherein the solid matrix does not comprise a hydrophilic or hydrophobic polymer. In embodiments, the ophthalmic drug is difluprednate.

In embodiments, the liquid surfactant is selected from polysorbate or tyloxapol and the solid surfactant is selected from a span (e.g. sorbitan) or a BRIJ (e.g., a surfactant comprising an ethylene, polyethylene or polyoxyethylene moiety) surfactant. In embodiments, the total surfactant is present in the solid matrix from about 25 to about 60% (w/w). In certain embodiments, the difluprednate is present in the solid matrix from about 40 to 75% (w/w). In embodiment, wherein the solid matrix sustained release ophthalmic formulation for topical delivery of an ophthalmic drug does not comprise a hydrophilic polymer, the hydrophilic polymer is selected from polyethylene glycol (PEG) polymers, acrylate-derivatized PEG (PEGDA) polymers, polysaccharide polymers, hydrophilic polyanhydrides or a combination thereof. In certain other embodiments, wherein the solid matrix sustained release ophthalmic formulation for topical delivery of an ophthalmic drug does not comprise a hydrophobic polymer, the hydrophobic polymer is selected from polyester, polycaprolactone, poly(D,L-lactic-co-glycolic acid)(PLGA), poly lactic acid (PLA), polyurethane, poly glycolic acid (PGA) or a combination thereof. It is understood the surfactant may comprise hydrophilic (or hydrophobic) monomers or moieties that are not excluded by way of exclusion of a hydrophilic or hydrophobic polymer.

In embodiments, the formulations are configured as a medical device including lacrimal implants, punctal plugs, intracanalicular plugs, or ocular rings. In embodiments, the formulations are configured for deposition within or adjacent to an eye. In certain embodiments, the medical device has a substantially cylindrical shape. In certain other embodiments, the medical device has a shape of a ring configured to be placed on a surface of an eye. In embodiments, the formulation further comprises a sheath body disposed at least partially over the matrix. In certain embodiments, the ophthalmic drug of the formulation is a powder, or insoluble or weakly soluble in water.

In certain embodiments, the solid matrix sustained release ophthalmic formulations do not comprise methacrylate polymers or monomers. In certain other embodiments, the solid matrix sustained release ophthalmic formulations do not comprise polysaccharide polymers.

In embodiments provided herein is a drug insert comprising a present solid matrix sustained release formulation as a drug core and an impermeable sheath body partially covering the drug core. In embodiments, the drug insert is manufactured by extruding an admixture of drug and polymer (e.g. present sustained release formulation) into the impermeable sheath, optionally cut to a desirable length and optionally sealing one end. In embodiments the drug inserts are cut to a length of about 0.95 inches and one end sealed with a medical grade adhesive.

In embodiments, the present drug insert is placed in a cavity of a lacrimal implant to form a drug delivery system. In embodiments provided herein is a lacrimal implant comprising a punctal plug comprising a plug body and a drug insert, wherein the insert comprises; a drug core comprising the present sustained release formulation, and an impermeable sheath body partially covering the drug core, wherein the sheath body is configured to provide an exposed proximal end of the drug core in direct contact with tear fluid that releases therapeutic agent to the eye when the drug insert is disposed within a channel of the punctal plug and the punctal plug is inserted into the lacrimal canaliculus of a patient.

In embodiments provided herein, the sustained release formulation, as a medical device, drug insert or drug delivery system, is used to deliver an ophthalmic drug to an eye for post-cataract surgery treatment. In embodiments provided herein is a method for delivering an anti-inflammatory drug (NSAID or steroidal anti-inflammatory drug) to the eye following cataract surgery, comprising, placing a lacrimal implant through a punctum and into a canalicular lumen of a patient, the implant comprising; a present solid matrix sustained release ophthalmic formulation, wherein the wherein the ophthalmic drug is a NSAID or steroidal anti-inflammatory drug and the matrix is configured for delivery of a daily therapeutic amount of the anti-inflammatory drug for a period of about 2 weeks to about one month.

In embodiments provided herein, the sustained release formulation, as a medical device, drug insert or drug delivery system, is used to deliver an ophthalmic drug to an eye for treatment of dry eye. In embodiments provided herein is a method for delivering a drug for dry eye treatment to the eye, comprising, placing a lacrimal implant through a punctum and into a canalicular lumen of a patient, the implant comprising; a present solid matrix sustained release ophthalmic formulation, wherein the wherein the ophthalmic drug is a Cyclosporine A and the matrix is configured for delivery of a daily therapeutic amount of Cyclosporine A for a period of at least 2 weeks and up to 6 months.

BRIEF DESCRIPTION OF THE DRAWINGS

In the drawings, like numerals describe similar components throughout the several views. Like numerals having different letter suffixes represent different instances of similar components. The drawings illustrate generally, by way of example, but not by way of limitation, various embodiments disclosed herein.

FIG. 3A provides a perspective view of an implant in accordance with an embodiment of the present invention.

FIG. 3B is a side view of an implant in accordance with an embodiment of the present invention.

FIG. 3C is a side view illustrating the second member and the third member of an implant in accordance with an embodiment of the present invention.

FIG. 3D is a back view of an implant in accordance with an embodiment of the present invention.

FIG. 3E is a cross-sectional view taken about line III(E)-III(E) of FIG. 3D depicting an implant with a bore, in accordance with an embodiment of the present invention.

FIG. 3F is a partially enlarged view of FIG. 3E taken about circle III(F) depicting the second member, the third member and a bore formed in the third member of an implant, in accordance with an embodiment of the present invention.

FIG. 4B is a cross-sectional view depicting an implant having a cavity formed in the second member, in accordance with an embodiment of the present invention.

FIG. 4C is a partially enlarged view taken about circle IV(C) of FIG. 4B depicting a cavity in the second member and a bore in the third member of an implant, in accordance with an embodiment of the present invention.

DETAILED DESCRIPTION OF THE INVENTION

Introduction

Figure 1:
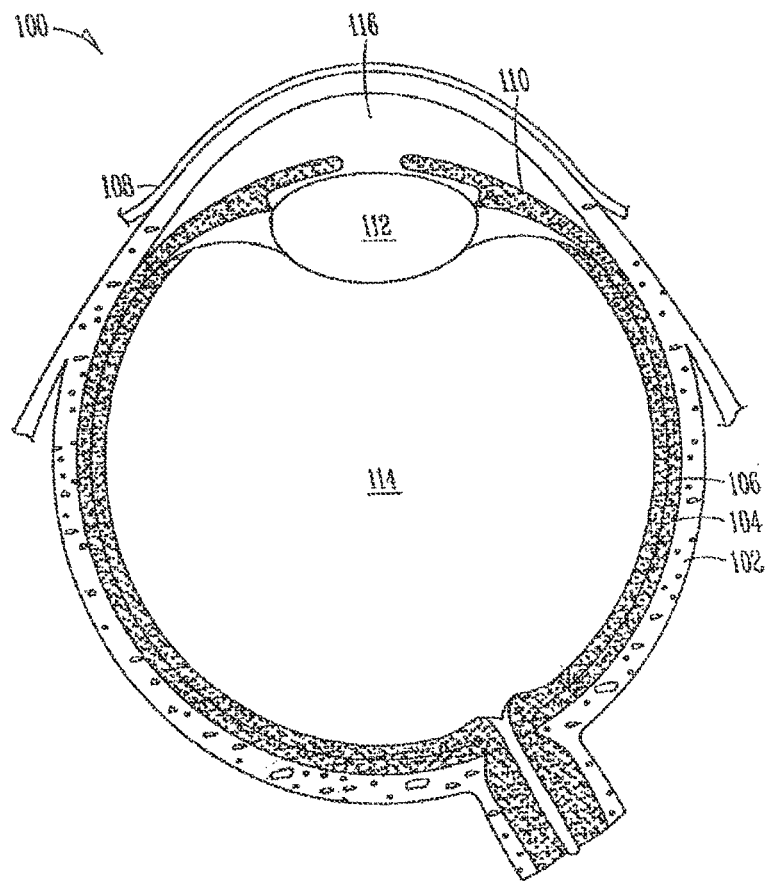
FIG. 1 illustrates an example of anatomical tissue structures associated with an eye, certain of these tissue structures providing a suitable environment in which a lacrimal implant can be used.

Provided herein are compositions, methods of manufacture and methods for the sustained topical delivery of an ophthalmic drug to an eye. In embodiments, the compositions comprise a solid matrix sustained release ophthalmic formulation for topical delivery of an ophthalmic drug to an eye for an extended period of time (e.g. at least two weeks and up to 6 months). In embodiments, the ophthalmic drug is a non-steroidal anti-inflammatory drug (NSAID), a steroidal non-inflammatory drug is a steroid or cyclosporine.

The present solid matrix sustained release ophthalmic formulations for topical delivery of an ophthalmic drug to an eye were empirically determined and configured for a daily sustained release at therapeutic levels of the ophthalmic drug for a treatment period of at least 2 weeks and up to 6 months. The treatment period and sustained release time period is dictated by the eye disease or treatment. For example, formulations comprising an anti-inflammatory drug for post-cataract surgery treatment need only be configured for daily therapeutic delivery for a treatment period of about 2 weeks to about 4 weeks. Other eye diseases or disorders, such as dry eye or glaucoma, require a longer treatment period such as at least one month and up to six months.

Actual dosage levels of the ophthalmic drugs in the drug delivery systems of use in the present invention may be varied to obtain an amount of the ophthalmic drugs that are effective to obtain a desired therapeutic response for a particular system and method of administration. The selected dosage level therefore depends upon such factors as, for example, the desired therapeutic effect, the route of administration, the desired duration of treatment, and other factors. The total daily dose of the ophthalmic drugs administered to a host in single or divided doses can vary widely depending upon a variety of factors including, for example, the body weight, general health, sex, diet, time and route of administration, rates of absorption and excretion, combination with other drugs, the severity of the particular condition being treated, etc. Generally, the amounts of the ophthalmic drug present in the drug delivery systems of the present invention can range from about 35% w/w to about 80% w/w and in embodiments from about 50% w/w to about 70% w/w.

In embodiments, the ophthalmic drugs are anti-inflammatory (steroid and non-steroid), drugs for the treatment of post-cataract surgery (e.g., pain, infection and/or inflammation), dry eye or drugs for the treatment of glaucoma. Examples of diseases or disorders that can be treated according to the methods of the invention with anti-inflammatory agents or cyclosporine include, but are not limited to, pre- and post-surgical ocular treatments, dry eye, anti-eye allergy, anti-infective, and post-surgical inflammation or pain. Additional diseases treatable by a method of the invention include but are not limited to, inflammatory mediated degeneration, post-surgical complications, damage associated with laser therapy including photodynamic therapy (PDT), surgical light induced iatrogenic retinopathy, post-cataract surgery and other ocular inflammatory diseases.

Figure 10:
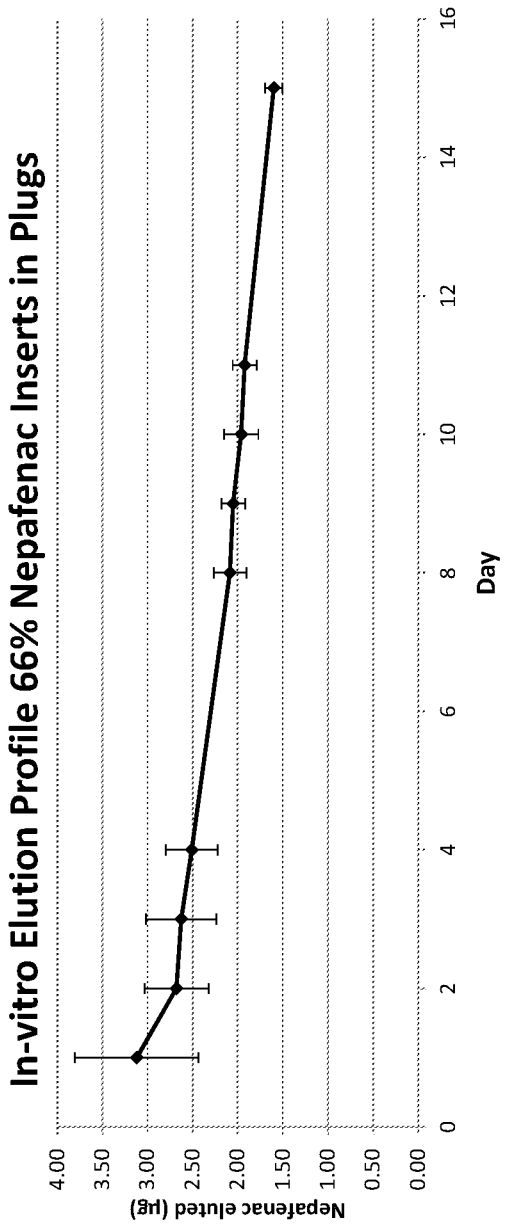
FIG. 10 provides an elution profile of a drug insert comprising nepafenac in a matrix comprising polycaprolactone, PEG 400 and tyloxapol.

In certain embodiments, the ophthalmic drug is the NSAID nepafenac. It was found that a solid matrix formulation comprising a combination of a hydrophilic polymer (e.g. low molecular weight PEG such as PEG 200 to 1000) and a hydrophobic polymer, such as polycaprolactone, wherein the hydrophobic polymer is present at a higher percentage (% w/w) than the hydrophilic polymer, and a nonionic surfactant, such as a polysorbate or tyloxapol, provided a daily elution of nepafenac between 3.5 μg and 1 μg over a treatment period of two weeks. That dose is therapeutic for the treatment of post-cataract surgery for pain and/or inflammation. In exemplary embodiments, the solid matrix sustained release ophthalmic formulation for topical delivery of nepafenac, comprises about 66% w/w of nepafenac; about 20% w/w of polycaprolactone; about 10% w/w PEG 400 polymers; and, about 4% w/w of a nonionic surfactant (e.g., polysorbate 80 or tyloxapol). See FIG. 10.

In certain embodiments, the ophthalmic drug is the steroidal anti-inflammatory drug difluprednate. It was found that a solid matrix formulation comprising drug and a combination of a nonionic solid (e.g. a sorbitan or polyethoxylated fatty alcohols, such as those sold under the tradename BRIJ) and liquid surfactants (e.g. polysorbates or tyloxapol), but no additional hydrophilic or hydrophobic polymers, provided a daily elution of difluprednate of at least 10 μg over a treatment period of about 2 weeks. That dose is therapeutic for the treatment of post-cataract surgery for pain and/or inflammation. In an exemplary embodiment, the solid matrix sustained release ophthalmic formulation for topical delivery of difluprednate, comprises about 40-60% (w/w) of difluprednate, 10-15% w/w of polysorbate 80 and about 30-45% w/w of Span 40 (Sorbitan monopalmitate). See Example 9.

Figure 12:
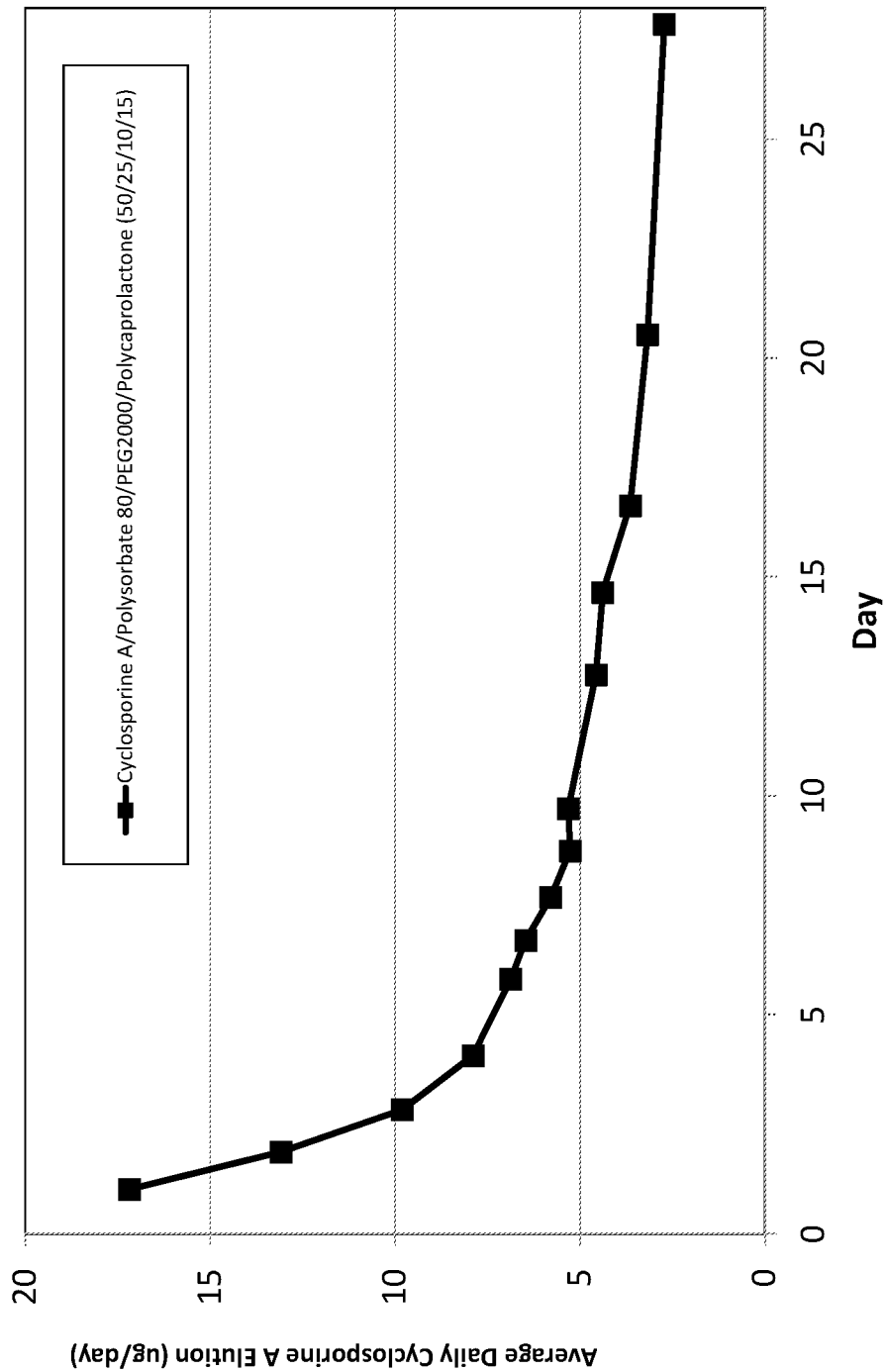
FIG. 12 provides an elution profile of a drug insert comprising Cyclosporine A in a matrix comprising PEG 2000 polymers, polycaprolactone and polysorbate 80.
Figure 13:
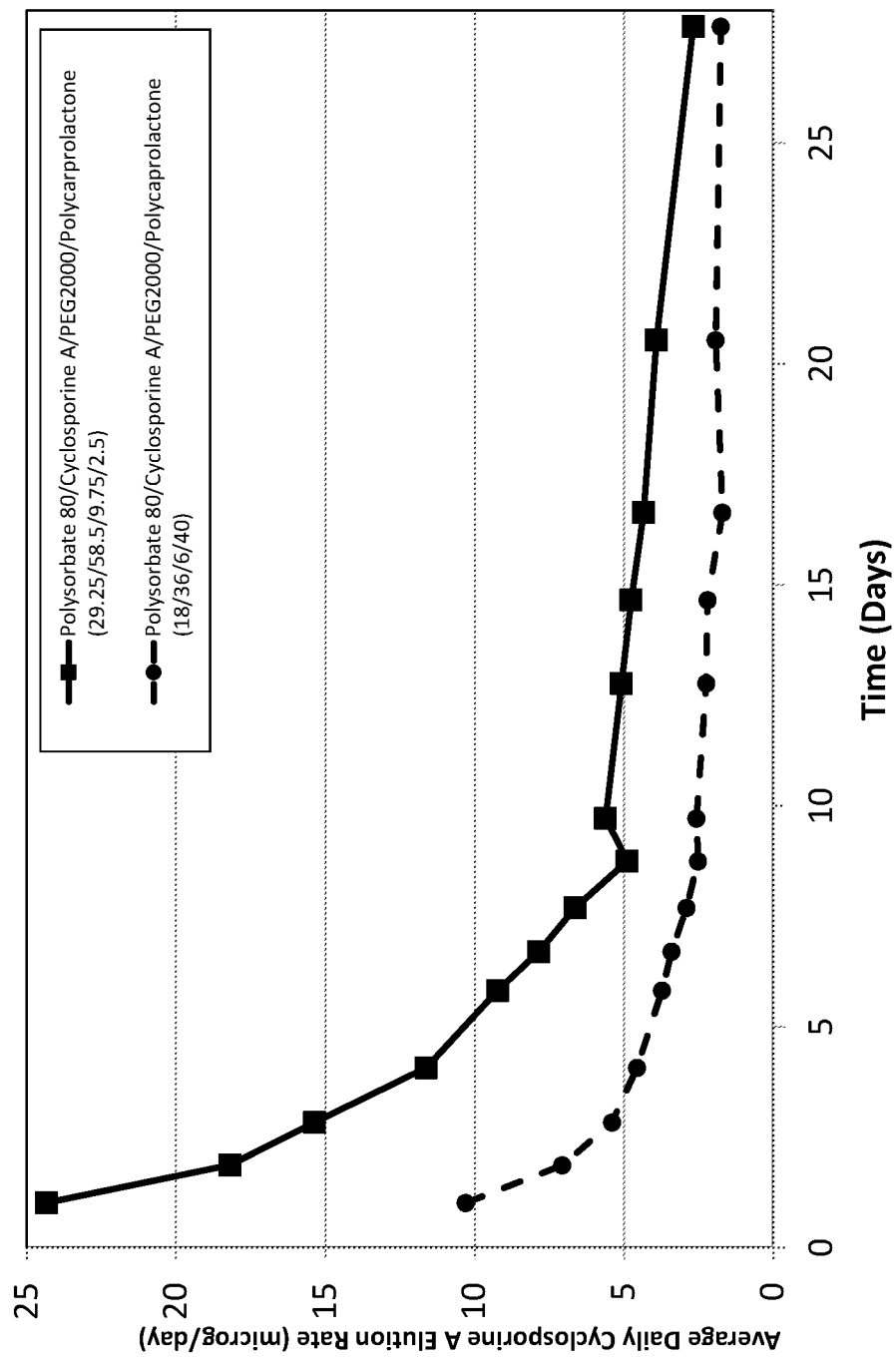
FIG. 13 provides an elution profile of a drug insert comprising Cyclosporine A in a matrix comprising PEG 2000 polymers, polycaprolactone and polysorbate 80.

In certain embodiments, the ophthalmic drug is cyclosporine. It was found that a solid matrix formulation comprising a combination of a hydrophilic polymer (e.g. high molecular weight PEG such as PEG 1000 to 20,000) and a hydrophobic polymer, such as polycaprolactone, and a nonionic surfactant, such as a polysorbate or tyloxapol, provided a daily elution of cyclosporine at least 2 μg, or between 17 μg and 3 μg over a treatment period of four weeks. That dose is therapeutic for the treatment of dry eye. In exemplary embodiments, the solid matrix sustained release ophthalmic formulation for topical delivery of cyclosporine, comprises 36-58.5% w/w of Cyclosporine A, 18-29.25% w/w of polysorbate 80, 2.5-40% w/w of polycaprolactone and about 6-9.75% w/w of PEG 2000 polymers. See FIGS. 12 and 13; and Example 11.

Definitions

As used herein, the terms "a" or "an" are used, as is common in patent documents, to include one or more than one, independent of any other instances or usages of "at least one" or "one or more."

As used herein, the term "or" is used to refer to a nonexclusive or, such that "A or B" includes "A but not B," "B but not A," and "A and B," unless otherwise indicated.

As used herein, the term "about" is used to refer to an amount that is approximately, nearly, almost, or in the vicinity of being equal to or is equal to a stated amount, e.g., the state amount plus/minus about 5%, about 4%, about 3%, about 2% or about 1%.

As used herein, an "axis" refers to a general direction along which a member extends. According to this definition, the member is not required to be entirely or partially symmetric with respect to the axis or to be straight along the direction of the axis. Thus, in the context of this definition, any member disclosed in the present application characterized by an axis is not limited to a symmetric or a straight structure.

In this document, the term "proximal" refers to a location relatively closer to the cornea of an eye, and the term "distal" refers to a location relatively further from the cornea and inserted deeper into a lacrimal canaliculus.

In the appended claims, the terms "including" and "in which" are used as the plain-English equivalents of the respective terms "comprising" and "wherein." Also, in the following claims, the terms "including" and "comprising" are open-ended, that is, a system, assembly, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Compositions

In embodiments, the composition comprises the present solid matrix sustained release formulation as a medical device, as a drug core, as a drug insert (e.g. present formulation and an outer layer or covering), and as a drug delivery system (e.g. drug insert or core and a body or retention element to maintain the drug insert or core in a desired location). In embodiments, the medical device (e.g. drug core or drug insert) may be placed in the lacrimal canaliculus or between a sclera tissue layer, such as between the surface of the eye and eye lid (e.g. an ocular ring placed outside the field of vision), or between a sclera tissue layer and a conjunctiva tissue layer of the eye to deliver the ophthalmic drug to the eye. In embodiments, the medical device comprises a substantially cylindrical diameter over the length of the medical device and may be configured for either placement in a lacrimal canaliculus (e.g. intracanalicular plug) or between an eyelid and the surface of the eye, which may be in the shape of a ring or linear. In alternative embodiments, the drug insert is adapted to be placed in a body of the drug delivery system. The ocular drug delivery system, disclosed in more detail below, uses a body that is interchangeable with a drug insert comprising different drugs and/or different matrix to provide topical sustained release of the drug.

In embodiments, the lacrimal implant of the invention is configured as a sustained release device, releasing the incorporated therapeutic agent in a therapeutically effective manner, e.g., at a rate that provides a therapeutically effective dosage for at least about 1 week, 2 weeks, 3 weeks, 4 weeks, 5 weeks, 6 weeks, 7 weeks, 8, weeks, 9 weeks 10 weeks, 11 weeks, or at least about 12 weeks or more. In an exemplary embodiment, the lacrimal implant is configured to be retained by the puncta for the duration of the intended controlled release of the therapeutic agent. In various embodiments, the duration of the intended controlled release of the therapeutic agent is at least about 1 week, 2 weeks, 3 weeks, 4 weeks, 5 weeks, 6 weeks, 7 weeks, 8, weeks, 9 weeks 10 weeks, 11 weeks, or at least about 12 weeks or more. In various embodiments at least 95% of the implanted implants are retained for the duration of the intended controlled release of the therapeutic agent. In an exemplary embodiment, the implant is retained by the puncta for a length of time to show therapeutic efficacy.

Ophthalmic Drugs

Generally, pharmaceutically active agents or drugs useful in the methods of the present invention can be any compound, composition of matter, or mixtures thereof that can be delivered from an implant (wherein the solid matrix sustained formulation is provided as a medical device), such as those described herein, to produce a beneficial and useful result to, for example, the eye, especially an agent effective in obtaining a desired local or systemic physiological or pharmacological effect.

Examples of such agents include, but are not limited to, anesthetics and pain killing agents such as lidocaine and related compounds, benzodiazepam and related compounds and the like; anti-fungal agents such as fluconazole and related compounds and the like; anti-viral agents such as trisodium phosphomonoformate, trifluorothymidine, acyclovir, ganciclovir, DDI, AZT and the like; cell transport/mobility impending agents such as colchicine, vincristine, cytochalasin B and related compounds and the like; antiglaucoma drugs (e.g. adrenergic agonists, adrenergic antagonists (beta blockers), carbonic anhydrase inhibitors (CAIs, systemic and topical), parasympathomimetics, prostaglandins and hypotensive lipids, and combinations thereof), antimicrobial agent (e.g., antibiotic, antiviral, antiparacytic, antifungal, etc.), a corticosteroid or other anti-inflammatory (e.g., an NSAID or other analgesic and pain management compounds), a decongestant (e.g., vasoconstrictor), an agent that prevents or modifies an allergic response (e.g., an antihistamine, cytokine inhibitor, leucotriene inhibitor, IgE inhibitor, immunomodulator), a mast cell stabilizer, cycloplegic, mydriatic or the like.

Other agents that can be incorporated into the solid matrix formulations in the invention include antihypertensives; decongestants such as phenylephrine, naphazoline, tetrahydrazoline and the like; immunological response modifiers such as muramyl dipeptide and related compounds and the like; peptides and proteins such as cyclosporine (including Cyclosporine A), insulin, growth hormones, insulin related growth factor, heat shock proteins and related compounds and the like; steroidal compounds such as corticosteroid, dexamethasone, difluprednate, triamcinolone, fluocinolone, cortisone, prednisolone or flumetholone and related compounds and the like; low solubility steroids such as fluocinolone acetonide and related compounds and the like; carbonic anhydrase inhibitors; diagnostic agents; antiapoptosis agents; gene therapy agents; sequestering agents; reductants such as glutathione and the like; antipermeability agents; antisense compounds; antiproliferative agents; antibody conjugates; antidepressants; bloodflow enhancers; antiasthmatic drugs; antiparasiticagents; non-steroidal anti inflammatory agents (NSAID) such as nepafenac, bromfenac, salicylate, indomethacin, ibuprofen, diclofenac, flurbiprofen, naproxen, piroxicam or nabumetone and the like; nutrients and vitamins: enzyme inhibitors: antioxidants; anticataract drugs; aldose reductase inhibitors; cytoprotectants; cytokines, cytokine inhibitors, and cytokin protectants; uv blockers; mast cell stabilizers; anti neovascular agents such as antiangiogenic agents, e.g., matrix metalloprotease inhibitors and the like.

Representative examples of additional pharmaceutically active agent for use herein include, but are not limited to, neuroprotectants such as nimodipine and related compounds and the like; antibiotics such as tetracycline, chlortetracycline, bacitracin, neomycin, polymyxin, gramicidin, oxytetracycline, chloramphenicol, gentamycin, erythromycin and the like; anti-infectives; antibacterials such as sulfonamides, sulfacetamide, sulfamethizole, sulfisoxazole; nitrofurazone, sodium propionate and the like; antiallergenics such as antazoline, methapyriline, chlorpheniramine, pyrilamine, prophenpyridamine and the like; anti-inflammatories such as hydrocortisone, hydrocortisone acetate, dexamethasone 21-phosphate, fluocinolone, medrysone, methylprednisolone, prednisolone 21-phosphate, prednisolone acetate, fluoromethalone, betamethasone, triminolone and the like; miotics; anti-cholinesterase such as pilocarpine, eserine salicylate, carbachol, di-isopropyl fluorophosphate, phospholine iodine, demecarium bromide and the like; miotic agents; mydriatics such as atropine sulfate, cyclopentolate, homatropine, scopolamine, tropicamide, eucatropine, hydroxyamphetamine and the like; svmpathomimetics such as epinephrine and the like; and prodrugs such as, for example, those described in Design of Prodrugs, edited by Hans Bundgaard, Elsevier Scientific Publishing Co., Amsterdam, 1985. In addition to the foregoing agents, other agents suitable for treating, managing, or diagnosing conditions in a mammalian organism may be entrapped in the copolymer and administered using the drug delivery systems of the current invention. Once again, reference may be made to any standard pharmaceutical textbook such as, for example, Remington's Pharmaceutical Sciences for pharmaceutically active agents.

Any pharmaceutically acceptable form of the foregoing therapeutically active agent may be employed in the practice of the present invention, e.g., the free base; free acid; pharmaceutically acceptable salts, esters or amides thereof, e.g., acid additions salts such as the hydrochloride, hydrobromide, sulfate, bisulfate, acetate, oxalate, valerate, oleate, palmitate, stearate, laurate, borate, benzoate, lactate, phosphate, tosylate, mesylate, citrate, maleate, fumarate, succinate, tartrate, ascorbate, glucoheptonate, lactobionate, and lauryl sulfate salts and the like; alkali or alkaline earth metal salts such as the sodium, calcium, potassium and magnesium salts and the like; hydrates; enantiomers; isomers; stereoisomers; diastereoisomers; tautomers; polymorphs, mixtures thereof, prodrugs thereof or racemates or racemic mixtures thereof.

Additional agents that can be used with the present methods utilizing lacrimal implants include, but are not limited to, drugs that have been approved under Section 505 of the United States Federal Food, Drug, and Cosmetic Act or under the Public Health Service Act, some of which can be found at the U.S. Food and Drug Administration (FDA) website http://www.accessdatalda.gov/scripts/cder/drugsatfda/index. Additional drugs include those listed in the Orange Book, either in paper or in electronic form, which can be found at the FDA Orange Book website (http://www.fda.gov/cder/ob/)), that has or records the same date as, earlier date than, or later date than, the filing date of this patent document. For example, these drugs can include, among others, dorzolamide, olopatadine, travoprost, bimatoprost, cyclosporine, brimonidine, moxifloxacin, tobramycin, brinzolamide, aciclovir timolol maleate, ketorolac tromethamine, prednisolone acetate, sodium hyaluronate, nepafenac, bromfenac, diclofenac, flurbiprofen, difluprednate, suprofenac, binoxan, patanol, dexamethasone/tobramycin combination, moxifloxacin, or acyclovir.

Examples of diseases or disorders that can be treated according to the methods of the invention with above-listed agents include, but are not limited to, glaucoma, pre- and post-surgical ocular treatments, dry eye, anti-eye allergy, anti-infective, post-surgical inflammation or pain, respiration-related disorders, such as allergies, inner ear disorders, such as dizziness or migraines, or other systemic disorders, such as hypertension, cholesterol management, pulmonary disorders or immunological disorders.

The solid matrix sustained release drug delivery systems of the present invention are particularly useful in the treatment of ophthalmic diseases, disorders and/or injuries. Representative examples of such ophthalmic diseases, disorders or injuries include, but are not limited to, diabetic retinopathy, glaucoma, macular degeneration, retinitis pigmentosa, retinal tears or holes, retinal-detachment, retinal ischemia, acute retinopathies associated with trauma, inflammatory mediated degeneration, post-surgical complications, damage associated with laser therapy including photodynamic therapy (PDT), surgical light induced iatrogenic retinopathy, drug-induced retinopathies, autosomal dominant optic atrophy, toxic/nutritional amblyopias; leber's hereditary optic neuropathy (LHOP), other mitochondrial diseases with ophthalmic manifestations or complications, angiogenesis; atypical RP; bardet-biedl syndrome; blue-cone monochromacy; cataracts; central areolar choroidal dystrophy; choroideremia; cone dystrophy; rod dystrophy; cone-rod dystrophy; rod-cone dystrophy; congenital stationary night blindness; cytomegalovirus retinitis; diabetic macular edema; dominant drusen; giant cell arteritis (GCA); goldmann-favre dystrophy; graves' ophthalmopathy; gyrate atrophy; hydroxychloroquine; iritis; juvenile retinoschisis; kearns-sayre syndrome; lawrence-moon bardet-biedl syndrome; leber congenital amaurosis; lupus-induced cotton wool spots; macular degeneration, dry form; macular degeneration, wet form; macular drusen; macular dystrophy; malattia leventinese; ocular histoplasmosis syndrome; oguchi disease; oxidative damage; proliferative vitreoretinopathy; refsum disease; retinitis *punctata albescens*; retinopathy of prematurity; rod monochromatism; RP and usher syndrome; scleritis; sector RP; sjogren-larsson syndrome; sorsby fundus dystrophy; stargardt disease and other retinal diseases.

In embodiments, the ophthalmic drug is a non-steroidal anti-inflammatory drug (NSAID) selected from Nepafenac, Bromfenac, salicylate, indomethacin, ibuprofen, diclofenac, flurbiprofen, naproxen, piroxicam or nabumetone; a steroidal anti-inflammatory drug selected from corticosteroid, dexamethasone, difluprednate, triamcinolone acetonide, triamcinolone, fluocinolone, cortisone, prednisolone or flumetholone, an anti-glaucoma drug or cyclosporine.

In embodiments, the present solid matrix sustained release ophthalmic formulations comprise from about 50% to about 80% w/w, from about 60% to about 70% w/w, or from about 64% to about 68% w/w of the ophthalmic drug. In embodiments, the ophthalmic drug is a NSAID such as nepafenac. In exemplary embodiments, the present solid matrix sustained release ophthalmic formulations comprise from about 64% to about 68% w/w of nepafenac.

In embodiments, the present solid matrix sustained release ophthalmic formulations comprise from about 35 to about 65% (w/w), from about 35% to about 60% w/w, from about 35% to about 55% w/w, from about 35% to about 50% w/w, or from about 35% to about 45% w/w of the ophthalmic drug. In other embodiments, the present solid matrix sustained release ophthalmic formulations comprise from about 40% to about 65% w/w, to about 45% to about 65% w/w, from about 50% to about 65% w/w, or from about 55% to about 65% w/w of the ophthalmic drug. In certain other embodiments, the present solid matrix sustained release ophthalmic formulations comprise about 35%, about 37.5%, about 40%, about 42.5%, about 45%, about 47.5%, about 50%, about 52.5%, about 55%, about 57.5%, about 60%, about 62.5%, or about 65% w/w of the ophthalmic drug. In embodiments, the ophthalmic drug is cyclosporine.

In embodiments, the present solid matrix sustained release ophthalmic formulations comprise from about 40 to about 75% (w/w), from about 40% to about 70% w/w, from about 40% to about 65% w/w, from about 40% to about 60% w/w, from about 40% to about 55% w/w, or from about 40% to about 50% w/w of the ophthalmic drug. In other embodiments, the present solid matrix sustained release ophthalmic formulations comprise from about 45% to about 75% w/w, from about 50% to about 75% w/w, from about 55% to about 75% w/w, or from about 60% to about 75% w/w of the ophthalmic drug. In certain other embodiments, the present solid matrix sustained release ophthalmic formulations comprise about 35%, about 37.5%, about 40%, about 42.5%, about 45%, about 47.5%, about 50%, about 52.5%, about 55%, about 57.5%, about 60%, about 62.5% or about 65% w/w of the ophthalmic drug. In embodiments, the ophthalmic drug is a steroidal non-inflammatory drug such as diflupredante.

In embodiments, the solid matrix sustained release ophthalmic formulation for topical delivery of the ophthalmic drugs disclosed above are used for the treatment of dry eye, glaucoma or post-cataract surgery, such as for pain and inflammation.

In embodiments, the formulation is prepared by dissolving the drug and polymer mixture or surfactants and then forming into a desired shape. In embodiments, the formulation is extruded into a sheath body to form a drug insert, which may be used with a lacrimal implant or device (e.g. drug delivery system). In other embodiments, the drug core or drug insert does not comprise a sheath body.

Solid Matrix Components

In embodiments, the present solid matrix sustained release ophthalmic formulations comprise a hydrophilic polymer. As used herein, the term "hydrophilic" is understood to be a polymer that has a strong affinity for water and may be readily soluble in water. For example, hydrophilic polymers may be polar and their interaction with water (and other polar) substances are more thermodynamically favorable than interactions with hydrophobic polymers or substances. In embodiments, hydrophilic polymers include for example, polar polymers, polysaccharides including alginate and chitosan, hydrophilic polyanhydrides, polyethylene glycol (PEG) proteins, DNA, and polyvinyl alcohol. In certain embodiments, hydrophilic polymer comprises polyethylene glycol (PEG) polymers, acrylate-derivatized PEG (PEGDA) polymers, polysaccharide polymers, hydrophilic polyanhydrides or a combination thereof.

As used herein, the PEG polymers (polymer of ethylene oxide, which may be branched, liner or derivatized with other moieties) may be referred to by their average molecular weight, e.g. 20,000 daltons (Da), which would be PEG 20,000. In embodiments, the PEG polymers comprise PEG 200 to about PEG 20,000. It is understood that polymers are not always monodispersed and the weight may indicate their average molecular weights. Moreover, the PEG used may comprise a distribution of molecular weights (polydisperse), wherein the size distribution can be characterized by its weight average molecular weight (Mw) or its number average molecular weight (Mn). It is understood that the PEG polymers disclosed herein with a molecular weight number (e.g. PEG 400 or PEG 2000) are an average molecular weight.

PEG polymers are liquids or low-melting solids depending on their molecular weight. Generally, PEG 1000, or less are liquid at room temperature (e.g. 20-25° C.). In certain embodiments, the PEG polymers are liquid between 20 and 25° C. In certain embodiments, the PEG polymers comprise PEG 200 to about PEG 1000. In exemplary embodiments, the PEG polymers comprise PEG 400. In certain embodiments, when PEG 200 to PEG 1000 is used in the present solid matrix sustained release ophthalmic formulations, the formulation further comprises a hydrophobic polymer (disclosed in more detail below) that is present at a higher percentage (% w/w) than the hydrophilic polymer.

In embodiments, the present solid matrix sustained release ophthalmic formulations comprise a low molecular weight PEG (e.g. PEG 200 to PEG 1000) that is present in the solid matrix at, or less than, 15% (w/w). In certain embodiments, the PEG polymer is present from about 5 to about 15% (w/w). In embodiments, wherein the low molecular weight PEG is present in the solid matrix at, or less than, 15% (w/w) the hydrophilic PEG polymers are admixed with a hydrophobic polymer that is present in the solid matrix at, or greater than 15% (w/w). In exemplary embodiments, the present solid matrix sustained release ophthalmic formulations comprise PEG 400 at about 10% w/w and a hydrophobic polymer at about, or greater than 15% (w/w). In embodiments, the present solid matrix sustained release ophthalmic formulations comprise a low molecular weight PEG (e.g. PEG 200 to PEG 1000) that is present in the solid matrix at about 5%, about 6%, about 7%, about 8%, about 9%, about 10%, about 11%, about 12%, about 13%, about 14% or about 15% w/w. The % numbers are inclusive of 0.5% above and below each of the whole percentage numbers, providing a range for "about". For example, about 10% is inclusive of 9.5, 9.75, 10, 10.25, 10.50 and each value in between thereof.

In exemplary embodiments, the present solid matrix sustained release ophthalmic formulations comprise nepafenac from about 60 to about 70% (w/w), polycaprolactone from about 30 to about 15% (w/w), PEG 400 from about 5 to about 15% (w/w) and a nonionic surfactant from about 1 to about 15% w/w.

In other embodiments, PEG polymers with a molecular weight greater than 1000 Da are used. Generally, about PEG 1000 to about PEG 20,000 are a solid at room temperature. In certain embodiments, the PEG polymers comprise PEG 1000 to about PEG 20,000. In exemplary embodiments, the PEG polymers comprise PEG 2000. In certain embodiments, when PEG 1000 to PEG 20,000 is used in the present solid matrix sustained release ophthalmic formulations, the formulation further comprises a hydrophobic polymer (disclosed in more detail below) that may be present at a higher percentage (% w/w), a lower percentage (% w/w), or the same, as the hydrophilic polymer.

In embodiments, the present solid matrix sustained release ophthalmic formulations comprise a high molecular weight PEG (e.g. PEG 1000 to PEG 20,000) that is present in the solid matrix from about 5 to about 15% (w/w). In embodiments, the present solid matrix sustained release ophthalmic formulations comprise a high molecular weight PEG (e.g. PEG 1000 to PEG 20,000) that is present in the solid matrix at about 5%, about 6%, about 7%, about 8%, about 9%, about 10%, about 11%, about 12%, about 13%, about 14% or about 15%. The % numbers are inclusive of 0.5% above and below each of the whole percentage numbers, providing a range for "about". For example, about 10% is inclusive of 9.5, 9.75, 10, 10.25, 10.50 and each value in between thereof.

In embodiments, the present solid matrix sustained release ophthalmic formulations comprise a hydrophobic polymer. The term "hydrophobic" as used herein is generally understood to be a polymer that has a limited affinity for water and does not mix well with water. For example, hydrophobic polymers may be non-polar and will aggregate in an aqueous solution and exclude water molecules. The exclusion of water maximizes the hydrogen bonding of the hydrophobic polymer, either to other hydrophobic polymers, a hydrophilic polymer or possibly even a surfactant. In embodiments, hydrophobic polymers include for example, non-polar polymers, polyester polymers, PLGA, PLA, polycaprolactone, and polyanhydrides with hydrophobic co-monomer (e.g. carboxyphenoxypropane). In certain embodiments, hydrophobic polymer is selected from polyester, polycaprolactone, poly(D,L-lactic-co-glycolic acid) (PLGA), poly lactic acid (PLA), polyurethane, poly glycolic acid (PGA) or a combination thereof. In exemplary embodiments, the hydrophobic polymer comprises polycaprolactone.

In embodiments, the present solid matrix sustained release ophthalmic formulations comprise a hydrophobic polymer and a hydrophilic polymer, wherein the hydrophobic polymer is present at or greater than 15% w/w, or from about 15 to about 30% (w/w). In embodiments, the hydrophilic polymer comprises low molecular weight PEG polymers. In certain embodiments, the present solid matrix sustained release ophthalmic formulations comprise about 15%, about 16%, about 17%, about 18%, about 19%, about 20%, about 21%, about 22%, about 23%, about 24%, about 25%, about 26%, about 27%, about 28%, about 29% or about 30% (w/w) of the hydrophobic polymer. The % numbers are inclusive of 0.5% above and below each of the whole percentage numbers, providing a range for "about". For example, about 20% is inclusive of 19.5, 19.75, 20, 20.25, 20.50% (w/w) and each value in between thereof. In exemplary embodiments, the hydrophobic polymer comprises polycaprolactone.

In alternative embodiments, the present solid matrix sustained release ophthalmic formulations comprise a hydrophobic polymer and a hydrophilic polymer, wherein the hydrophobic polymer is present from about 2.5 to about 40% (w/w). In embodiments, the hydrophilic polymer comprises high molecular weight PEG polymers. In certain embodiments, the present solid matrix sustained release ophthalmic formulations comprise about 2.5%, about 5%, about 7.5%, about 10%, about 12.5%, about 15%, about 17.5%, about 20%, about 22.5%, about 25%, about 27.5%, about 30%, about 32.5%, about 35%, about 37.5%, or about 40% (w/w) of the hydrophobic polymer. The % numbers are inclusive of 1.25% above and below each of the percentage numbers, providing a range for "about". For example, about 5% is inclusive of 3.75, 4.5, 5, 5.5, 6.25% (w/w) and each value in between thereof. In exemplary embodiments, the hydrophobic polymer comprises polycaprolactone.

In embodiments, the present solid matrix sustained release ophthalmic formulations comprise a nonionic surfactant. As used herein "surfactant" refers to a compound that lowers the surface tension between two liquids or between a liquid and a solid. Surfactants are typically amphiphilic, meaning they comprise both a hydrophilic moiety and a hydrophobic moiety, such as fatty alcohol groups and compounds that form micelles in an aqueous solution. Nonionic surfactants have covalently bonded oxygen-containing hydrophilic groups, which are bonded to hydrophobic parent structures; an amphiphilic compound. The water-solubility of the oxygen groups is the result of hydrogen bonding. The differences between the individual types of nonionic surfactants are slight, and the choice is primarily governed based on the costs of special properties, e.g., effectiveness and efficiency, toxicity, dermatological compatibility and biodegradability, or permission for use in pharmaceutical products. In the instant solid matrix sustained release ophthalmic formulations, the choice of an individual surfactant may also be governed by improved efficiency in manufacturing, e.g. extrusion of the formulation into a mold or tubing, such as a sheath body. For example, use of tyloxapol or polysorbate provides little difference in daily elution rate, however one may provide for improved extrusion during manufacturing depending on the choice of hydrophobic and hydrophilic polymers and their overall % w/w in the matrix. In certain exemplary embodiments, the present solid matrix sustained release ophthalmic formulations comprise tyloxapol. In other exemplary embodiments, solid matrix sustained release ophthalmic formulations comprise a polysorbate surfactant such as polysorbate 80.

Examples of nonionic surfactants include fatty alcohol ethoxylates, alkylphenol ethoxylates, fatty acid ethoxylates (e.g. polysorbate), certain ethoxylated fatty esters and oils, ethoxylated amines and/or fatty acid amides, terminally blocked ethoxylates, fatty acid esters of polyhydroxy compounds, fatty acid esters of glycerol, fatty acid esters of sorbitol (e.g. Spans), fatty acid esters of sucrose, alkyl polyglucosides, amine oxides, sulfoxides, polymers of alkyl aryl polyether alcohol (e.g. tyloxapol), polyoxyethylene ethers (e.g. BRIJ compounds) and phosphine oxides.

Polysorbate surfactants are ethoxylated sorbitan esters and include polysorbate 20 (polyoxyethylene (20) sorbitan monolaurate), polysorbate 40 (polyoxyethylene (20) sorbitan monopalmitate), polysorbate 60 (polyoxyethylene (20) sorbitan monostearate), polysorbate 60 (polyoxyethylene (20) sorbitan monostearate), and polysorbate 80 (polyoxyethylene (20) sorbitan monooleate), wherein the number 20 following the 'polyoxyethylene' part refers to the total number of oxyethylene—($CH_2CH_2O$)— groups found in the molecule. The number following the 'polysorbate' part is related to the type of fatty acid associated with the polyoxyethylene sorbitan part of the molecule. Monolaurate is indicated by 20, monopalmitate is indicated by 40, monostearate by 60, and monooleate by 80. In exemplary embodiments, the present solid matrix sustained release ophthalmic formulations comprise the nonionic surfactant polysorbate 80.

BRIJ nonionic surfactants are polyoxyethylene ethers and include, polyoxyethylene (20) oleyl ether, polyoxyethylene (10) oleyl ether, polyoxyethylene (2) oleyl ether, polyoxyethylene (100) stearyl ether, polyoxyethylene (20) cetyl ether, polyoxyethylene (10) cetyl ether, polyoxyethylene (10) stearyl ether, polyoxyethylene (4) lauryl ether, polyoxyethylene (20) stearyl ether, polyoxyethylene (2) cetyl ether, and polyoxyethylene (2) stearyl ether.

Span nonionic surfactants are sorbitan esters that include sorbitan oleate, sorbitan stearate, sorbitan laurate, sorbitane trioleate, sorbitan tristearate, sorbitan sesquioleate, and sorbitan monopalmitate. In embodiments, the present solid matrix sustained release ophthalmic formulations comprise the nonionic surfactant sorbitan ester. In certain embodiments, the present solid matrix sustained release ophthalmic formulations comprise a combination of the nonionic surfactants sorbitan ester (e.g. Span 40) and polysorbate (e.g. polysorbate 80). In certain embodiments, the present solid matrix sustained release ophthalmic formulations comprise a combination of the nonionic surfactants sorbitan ester (e.g. Span 40) and polysorbate (e.g. polysorbate 80), wherein the solid matric does not comprise a hydrophilic or hydrophobic polymer as disclosed above.

The surfactants used herein may be in a liquid form or a solid form. We have found, particularly for difluprednate, that a combination of a solid and a liquid surfactant provided desirable daily elution rates wherein the formulation did not comprise a hydrophilic or hydrophobic polymer beyond the amphiphilic compound(s) provided as the surfactants. In particular a combination of sorbitan ester surfactants (Span) and ethoxylated sorbitan esters (polysorbates) provided desirable daily elution rates of the drug (e.g. difluprednate). In embodiments, the present solid matrix sustained release ophthalmic formulations comprise about 10 to 15% w/w of polysorbate and about 30-40% w/w of sorbitan ester surfactants.

In certain embodiments, the present solid matrix sustained release ophthalmic formulations comprise from about 1% to about 10% w/w of a nonionic surfactant. In embodiments, the nonionic surfactant is present in the solid matrix formulation at about 1%, about 2%, about 3%, about 4%, about 5%, about 6%, about 7%, about 8%, about 9% or about 10% (w/w). The % numbers are inclusive of 0.5% above and below each of the whole percentage numbers, providing a range for "about". For example, about 4% is inclusive of 3.5, 3.75, 4, 4.25, 4.50 and each value in between thereof. In certain embodiments, the present solid matrix sustained release ophthalmic formulations further comprise a hydrophilic polymer and a hydrophobic polymer. In exemplary embodiments, the nonionic surfactant is a polysorbate or tyloxapol.

In alternative embodiments, the present solid matrix sustained release ophthalmic formulations comprise from about 15% to about 30% w/w of a nonionic surfactant. In embodiments, the nonionic surfactant is present in the solid matrix formulation at about 15%, about 16%, about 17%, about 18%, about 19%, about 20%, about 21%, about 22%, about 23%, about 24%, about 25%, about 26%, about 27%, about 28%, about 29% or about 30% (w/w). The % numbers are inclusive of 0.5% above and below each of the whole percentage numbers, providing a range for "about". For example, about 20% is inclusive of 19.5, 19.75, 20, 20.25, 20.50 and each value in between thereof. In certain embodiments, the present solid matrix sustained release ophthalmic formulations further comprise a hydrophilic polymer and a hydrophobic polymer. In exemplary embodiments, the nonionic surfactant is a polysorbate or tyloxapol.

In certain embodiments, the present solid matrix sustained release ophthalmic formulations comprise a nonionic surfactant selected from tyloxapol, sorbitan esters, polyoxyethylene ethers, a polysorbate or a combination thereof.

In embodiments, at the time of manufacture and before the present solid matrix sustained release ophthalmic formulation is placed for delivery of the ophthalmic drug, the solid matrix formulation contains less than 10% water (w/v), or less than 5% or less than 1% water (w/v). In certain embodiments, the solid matrix formulation contains about 1% water, about 2% water, about 3% water, about 4% water, about 5% water, about 6% water, about 7% water, about 8% water, or about 9% water (w/v). In certain embodiments, the solid matrix formulation contains about 1% to about 10%, about 2% to about 10%, about 3% to about 10%, about 4% to about 10%, about 5% to about 10% or about 6% to about 10% water (w/v). In certain embodiments, the solid matrix formulation contains about 1% to about 9%, about 1% to about 8%, about 1% to about 7%, about 1% to about 6%, about 1% to about 5% or about 1% to about 4% water (w/v).

Lacrimal Implants

In embodiments, provided herein are lacrimal implants comprising a punctal plug comprising a plug body and a drug insert, wherein the insert comprises; a drug core comprising any one of the present solid matrix sustained release ophthalmic formulations disclosed herein; and, an impermeable sheath body partially covering the drug core, wherein the sheath body is configured to provide an exposed proximal end of the drug core in direct contact with tear fluid that releases an ophthalmic drug to the eye when the drug insert is disposed within a channel of the punctal plug and the punctal plug is inserted into the lacrimal canaliculus of a patient.

In certain embodiments, the any one of the present solid matrix sustained release ophthalmic formulations disclosed herein are configured as a medical device for the delivery of the ophthalmic drug to the eye. Those medical devices may take the shape of a depot, a lacrimal implant with a separate body, an intracanalicular plug that does not further comprise a separate plug body or a sheath body, an ocular ring (such as one that is placed on the eye surface but under the eye lid), or a contact lens. In certain embodiments, the intracanalicular plug comprises a polymeric coating or layer completely or partially surrounding the plug. In embodiments, the medical device may comprise a coating or an internal filament to provide structural integrity to the medical device. In embodiments, the medical device has a substantially cylindrical shape wherein the diameter of the entire medical device is approximately the same at the time of placement in, on or near the eye.

In certain embodiments, the compositions of the invention comprise an implant including a distinct solid matrix formulation drug core or integrated drug or other agent disposed in at least one of the first member 305 or the second member 310 of the implant body, to provide a sustained release of a therapeutic agent (used interchangeably herein with ophthalmic drug). For instance, the drug core or integrated drug or other agent disposed may be disposed in the cavity 458 of the lacrimal implant 400 to provide a sustained drug or other therapeutic agent release.

An exemplary implant of use in the methods of the invention is configured to deliver a therapeutic agent to one or more of an eye, nasal passage or inner ear system. In various embodiments, the drug is delivered systemically to the subject through the eye. A therapeutic agent core can comprise one or more therapeutic agents, and in some examples, one or more matrix materials to provide sustained release of the drug or other agents.

In various embodiments, the drug core (used interchangeably herein with the present solid matrix sustained release ophthalmic formulation) is inserted into cavity 458.

In embodiments, the compositions comprise a drug insert comprising a sheath body and a present sustained release ophthalmic formulation. The sheath body can comprise appropriate shapes and materials to control the migration of anti-inflammatory agent from the drug core. In some embodiments, the sheath body houses the drug core and can fit snugly against the core. The sheath body is made from a material that is substantially impermeable to the anti-inflammatory agent so that the rate of migration of the agent may be largely controlled by the exposed surface area of the drug core that is not covered by the sheath body. In many embodiments, migration of the anti-inflammatory agent through the sheath body can be about one tenth of the migration of anti-inflammatory agent through the exposed surface of the drug core, or less, often being one hundredth or less. In other words, the migration of the anti-inflammatory agent through the sheath body is at least about an order of magnitude less that the migration of anti-inflammatory agent through the exposed surface of the drug core. Suitable sheath body materials include polyimide, polyethylene terephthalate (hereinafter "PET"). The sheath body has a thickness, as defined from the sheath surface adjacent the core to the opposing sheath surface away from the core, from about 0.00025" to about 0.0015". The total diameter of the sheath that extends across the core ranges from about 0.2 mm to about 1.2 mm. The core may be formed by dip coating the core in the sheath material. Alternatively or in combination, the sheath body can comprise a tube and the core introduced into the sheath, for example as a liquid or solid that can be slid, injected or extruded into the sheath body tube. The sheath body can also be dip coated around the core, for example dip coated around a pre-formed core.

It is generally understood that when the present solid matrix formulation is at least partially surrounded by a sheath body, the hydrophobic or hydrophilic polymers do not erode. In other words, they are not biodegradable via hydrolysis or oxidation, even when those polymers may be biodegradable under different conditions (e.g., when not protected by a sheath body). Hence, while hydrophilic moieties present in the polymers and/or surfactants of the present solid matrix sustained release ophthalmic formulations may bind water molecules, such as present in tear fluid, the polymers do not generally undergo hydrolysis during the treatment period.

The sheath body can be provided with additional features to facilitate clinical use of the implant. For example, the sheath may receive a drug core that is exchangeable while the implant body, retention structure and sheath body remain implanted in the subject. The sheath body is often rigidly attached to the retention structure as described above, and the core is exchangeable while the retention structure retains the sheath body. In specific embodiments, the sheath body can be provided with external protrusions that apply force to the sheath body when squeezed and eject the core from the sheath body. Another drug core can then be positioned in the sheath body. In many embodiments, the sheath body or retention structure may have a distinguishing feature, for example a distinguishing color, to show placement such that the placement of the sheath body or retention structure in the canaliculus or other body tissue structure can be readily detected by the subject. The retention element or sheath body may comprise at least one mark to indicate the depth of placement in the canaliculus such that the retention element or sheath body can be positioned to a desired depth in the canaliculus based on the at least one mark.

FIGS. 3-6 illustrate exemplary embodiments of lacrimal implants of use with the present formulations and in methods of the invention. The exemplary implants are insertable through a lacrimal punctum 212, 214 and into its associated canaliculus 208, 210. Exemplary lacrimal implants of use in the present invention comprise a first member, a second member and a heel, such as the first member 305, the second member 310 and the third member or heel 330 depicted in FIG. 3A. Exemplary lacrimal implants further comprise a bore that is formed in the heel, for example, the bore 385 formed in the third member or heel 330 in FIG. 3A. In some embodiments, exemplary lacrimal implants further comprise a cavity 458 (e.g., lacrimal implants illustrated in FIG. 4A).

Referring to FIG. 3A, where a perspective view of an exemplary lacrimal implant 300 of use in the present methods is depicted, the first member 305 is characterized by a first axis A and the second member 310 is characterized by a second axis B.

The third member or heel 330 is configured to connect the first member 305 and the second member 310 at a first angle $\theta_1$, where $\theta_1$ is defined by the first axis A with respect to the second axis B. For instance, in FIG. 3A, the first angle $\theta_1$ refers to the angle originating at the first axis A and turning counterclockwise from the first axis A to the second axis B. In some embodiments, the first axis A and the second axis B are in the same plane and intersect each other. In some embodiments, the first axis A is in a plane other than the plane of the second axis B, and the first axis A and the second axis B do not intersect. In such embodiments, the first angle $\theta_1$ refers to the angle defined by a parallel line of the first axis A with respect to the second axis B. This parallel line of the first axis A lies in the same plane as the second axis and intersects with the second axis.

In some embodiments, the first angle $\theta_1$ is from about 30 degrees to about 150 degrees, from about 45 degrees to about 135 degrees, or from about 75 degrees to about 105 degrees. For example, in some embodiments, the first angle $\theta_1$ is approximately 90 degrees.

In some embodiments, the overall dimension of the implant along the first axis is from about 4 mm to about 8 mm. In an exemplary embodiment, the overall dimension along the first axis is about 5 mm to about 7 mm. In various embodiments, the overall dimension along the first axis is about 6.3 mm.

In various embodiments, the overall dimension along the second axis B is from about 1 mm to about 3 mm, e.g., from about 1.2 mm to about 1.9 mm.

In some embodiments, the overall dimension along the first axis is approximately 6.3 mm and the overall dimension along the second axis is approximately 1.2 mm. In various embodiments, the overall dimension along the first axis is approximately 6.3 mm and the overall dimension along the second axis is approximately 1.9 mm. In some embodiments, the overall dimension along the first axis is approximately 4.8 mm and the overall dimension along the second axis is approximately 1.9 mm.

Figure 2:
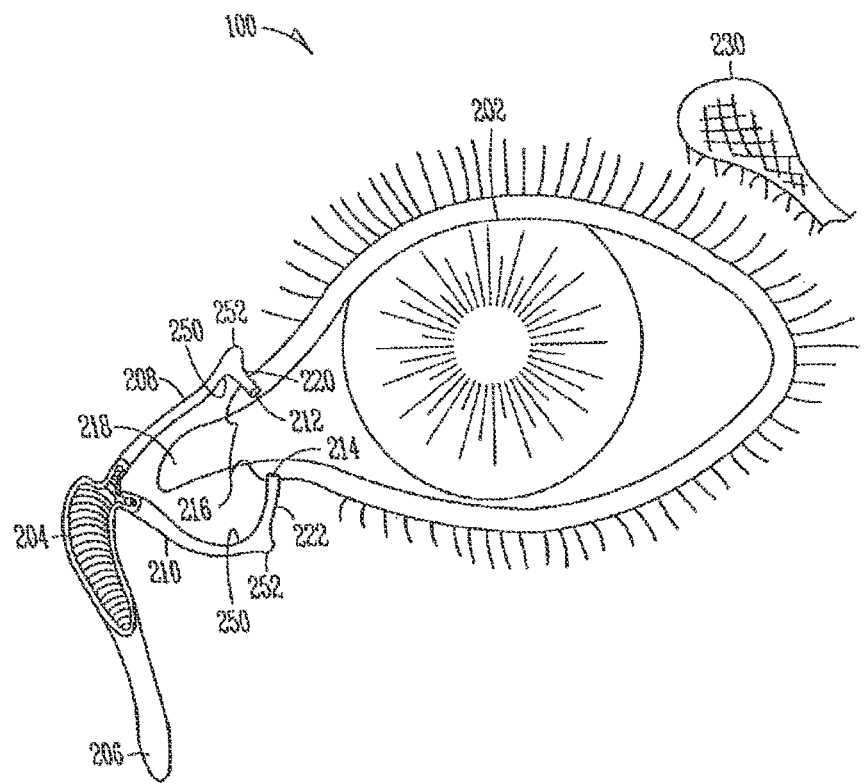
FIG. 2 illustrates another example of anatomical tissue structures associated with an eye, certain of these tissue structures providing a suitable environment in which a lacrimal implant can be used.

In some embodiments, the first member 305 is configured to extend into a canaliculus, while the second member 310 is configured to reside in the vertical portion 220, 222 of the canaliculus and to extend to the opening of, or out of the opening of, the associated puncta. When a lacrimal implant 300 of such configuration is inserted into a canaliculus, the intersection of the first axis A and the second axis B resides generally at a curvature of the canaliculus, such as the canaliculus curvature 250 in FIG. 2. In some embodiments, the first member 305 and the second member 310 are connected at the first angle, and that angle is at least about 45 degree, thereby forming an angled intersection between the first member and the second member. In various embodiments, when the lacrimal implant 300 is positioned in the lacrimal canaliculus, at least a portion of the angled intersection is biased against a canaliculus curvature of the lacrimal canaliculus. In this embodiment, the lacrimal implant 300 uses anatomical structures to facilitate the retention of the implanted lacrimal implant 300.

FIG. 3B depicts a side view of an exemplary lacrimal implant 300 of the invention. In some embodiments, the first member 305 includes an intermediate segment 315, a tip segment or tip 325, and a forward segment 320 in between the forward segment and tip segment. While the intermediate segment 315 is configured to be connected to the second member 310 by the third member or heel 330, the tip segment or tip 325 is configured to be inserted through a punctum prior to the other two segments of the first member 305 and prior to the other members of the lacrimal implant 300.

In some embodiments, the intermediate segment 315, the forward segment 320 and the tip segment or tip 325 are distinguishable from each other in general by their shapes. For example, in some embodiments, the intermediate segment 315 has a generally cylindrical shape with a diameter that is larger than the diameter of the tip segment or tip 325. In various embodiments, the forward segment 320 is tapered and has a conical shape, such that the forward segment 320 connects the intermediate segment 315 at one end and the tip segment or tip 325 at the other end. In some embodiments, the transition from the intermediate segment 315 to the forward segment 320 or the transition from the forward segment 320 to the tip segment or tip 325 is gradual and smooth such that no distinguishable edge exists at the transition.

In some embodiments, the intermediate segment 315 has a cylindrical shape. In various embodiments, the intermediate segment has a circular cross section, an elliptic cross section, or a polygonal cross section. The intermediate segment 315 is of any useful combination of length and diameter.

In some embodiments, the intermediate segment 315 has a diameter that is from about 0.4 mm to about 0.8 mm. For example, in some embodiments the diameter of the intermediate segment 315 is from about 0.53 mm to about 0.63 mm. In some embodiments, the intermediate segment 315 has a length along the first axis A that is from about 0.5 mm to about 3.5 mm. For example, in some embodiments the length of the intermediate segment 315 is from about 1 mm to about 2.8 mm.

In some embodiments, the tip segment or tip 325 is substantially a semi-sphere, or a portion of a semi-sphere. In exemplary embodiments, the semi-sphere, or portion therapy, has a radius that is from about 0.05 mm to about 0.3 mm. For example, in some embodiments, the radius of the tip segment or tip 325 is approximately 0.20 mm.

In some embodiments, the forward segment 320 has a conical configuration, tapering from the diameter of the intermediate segment 315 as it approaches the tip segment or tip 325. In some embodiments, the forward segment 320 is short and is tapered steeply, thus forming a wider taper angle. The forward segment 320 can also be long and tapered more gradually, thus forming a narrower taper angle. The tapering angle $\theta_3$ is illustrated in FIG. 3E. In some embodiments, the tapering angle $\theta_3$ is from about 2° to about 10°. For example, in some embodiments the tapering angle $\theta_3$ is from about 3.8° to about 7.8°. In some embodiments, $\theta_3$ is about 7.8°. In some embodiments, the forward segment 320 has a length along the first axis A that is from about 1 mm to about 5 mm. For example in some embodiments the length of forward segment 320 is from about 1.7 mm to about 3.5 mm.

Referring to FIG. 3B, in some embodiments of implants of use in the present method, the second member 310 includes an upright segment 335 that extends from the third member or heel 330 generally along the direction of the second axis B. In various embodiments, the second member 310 further includes a head segment 340 that attaches to the upright segment 335 at an end opposite to the third member or heel 330. In some embodiments, the second member 310 is configured such that the upright segment 335 resides in the vertical portion of the canaliculus while the head segment 340 contacts the tissue surrounding the exterior of the punctum when the lacrimal implant 300 is positioned in the lacrimal canaliculus. In an exemplary embodiment, illustrated in FIGS. 3A-3F, the upright segment 335 has a cylindrical shape and the head segment 340 has an oval or oblong configuration. However, it will be appreciated that any other suitable shapes or configurations can be used and are within the scope of the present invention. For example, in various embodiments, the upright segment 335 is configured to be a conical; the head segment 340 is configured to have a circular, elliptical or polygonal cross section.

In some embodiments, the upright segment 335 has a characteristic diameter that is from about 0.7 mm to about 0.9 mm. For example, in some embodiments, the characteristic diameter of the upright segment 335 is about 0.8 mm.

In some embodiments, the upright segment 335 has a length in the direction of the second axis B that is from about 0.7 mm to about 1.5 mm. For example, in some embodiments the length of upright segment 335 along the direction of the second axis B is about 0.9 mm.

Generally, the head segment 340 has a cross section characterized by a minor axis and a major axis. The minor axis and the major axis refer to the shortest characteristic diameter and the longest characteristic diameter of the cross section, respectively. As such, the minor axis is equal to or less than the major axis. For instance, in some embodiments where the head segment 340 has a circular cross section, the minor axis and the major axis are of equal length. In various embodiments, the head segment 340 has an oval or oblong cross section, and the minor axis is shorter than the major axis. In some embodiments, the head segment 340 is elongated in a direction that is parallel to the first axis A. The major axis indicates the extension of the first member 305 and facilitates positioning of the lacrimal implant 300 in the punctum and canaliculus. In some embodiments, the major axis is from about 1.5 mm to about 2.5 mm. In various embodiments, the minor axis is from about 1 mm to about 1.5 mm. For example, in some embodiments, the major axis and the minor axis head segment 340 are approximately 1.9 mm and 1.3 mm respectively. In some embodiments, the head segment 340 has a thickness in the direction of the second axis that is from about 0.2 mm to about 0.4 mm. For example, in some embodiments, the thickness of the head segment 340 in the direction of the second axis is approximately 0.3 mm.

Referring still to FIG. 3B, exemplary head segment 340 comprises an under-surface 350 facing towards the third member or heel 330 and an outer-surface 355 that faces away from the third member or heel 330. Exemplary head segment 340 further comprises an edge surface 345 that couples the under-surface 350 and the outer-surface 355. The distance between the under-surface 350 and the outer-surface 355 can be readily varied. In some embodiments, the distance is from about 0.2 mm to about 0.4 mm.

In some embodiments, the outer-surface 355 is smaller than the under-surface 350 and is substantially flat. In various embodiments, the edge surface 345 is tapered, curved, angular, or multifaceted. In some embodiments, the edge surface 345 has a radius of curvature that is from about 0.2 mm to about 0.7 mm. In some embodiments, the under-surface 350 is in general flat and is configured to contact the exterior tissue surrounding the punctum when the lacrimal implant 300 is positioned in the lacrimal canaliculus.

In some embodiments, the third member or heel 330 includes an upper surface 360 a lower surface 365 and side surfaces 370. In the illustrated embodiments, the bore 385 extends from the upper surface 360 into the third member or heel 330. In some embodiments, the upper surface 360 and the lower surface 365 are substantially flat and separated from each other by a distance. Such distance is readily variable and is typically about 0.3 mm to about 0.7 mm. For instance, in some embodiments, the upper surface 360 and the lower surface 365 are separated by a distance that is from about 0.4 mm to 0.6 mm (e.g., about 0.53 mm). In some embodiments, the upper surface 360 extends beyond the intersection with the second member 310. In some embodiments, the upper surface 360 extends beyond the intersection with the second member 310 for a distance that is from about 0.3 to about 0.6 mm. The upper surface 360 can also be joined with the side surfaces 370. In various embodiments, upper surface 360 and side surfaces 370 are joined by a curved intersection 380. In some embodiments, the curved intersection 380 has a radius of curvature that is from about 0.04 mm to about 0.08 mm.

Referring now to FIGS. 3D and 3F, in some embodiments, the third member or heel 330 includes a heel connecting segment 375 configured to couple the third member or heel 330 to the first member 305 or to the intermediate segment 315 of the first member 305. The heel connecting segment 375 is of readily variable shape, including flat or curved structures. In FIG. 3F, a width of the heel connecting segment 375 in the direction of the second axis B varies along the direction of the first axis A. For example, the heel connecting segment 375 has a smaller width at or near the side surfaces 370 than the diameter of the intermediate segment 315 of the first member 305. In some embodiments, at or near the intersection with the intermediate segment 315, the heel connecting segment 375 increases the width and thus forms a notch as depicted in FIG. 3F. It will be appreciated that the notch can be either deeper or shallower along both the first axis A and the second axis B before it meets the first member 305 or the second member 310.

A notch is not a required feature in the implants of the present invention. In some embodiments, the heel connecting segment 375 has the same dimension as the diameter of the intermediate segment 315. For example, the thickness of the third member or heel 330 along the second axis B is equal to the diameter of the intermediate segment 315 of the first member 305. For example, in some embodiments, both the thickness of the third member or heel 330 in the direction of the second axis B and the diameter of the intermediate segment 315 are from about 0.53 mm to about 0.63 mm. In such configurations, the third member or heel 330 couples with the intermediate segment 315 without forming a notch, as illustrated by the alternative heel connecting segment 675 in FIG. 6.

By way of illustration, the third member or heel 330 depicted in FIGS. 3A-3F is substantially parallel to the first axis A of the first member 305. It would be appreciated that this is unnecessary. In some embodiments, the third member or heel 330 can form an angle with relation to the first axis A.

Exemplary structures of the bore 385 are detailed in FIGS. 3E and 3F, where a cross sectional view and a partial enlarged cross sectional view of the lacrimal implant 300 are provided. The bore 385 is configured to receive a tip or other protrusion of an external insertion tool for facilitating insertion of the lacrimal implant 300 into a lacrimal punctum. The configuration, including size, shape, angle (θ2) and position of the bore in the heel are readily adjustable to facilitate the mating of the insertion tool with the bore, the flexibility of the heel, or the retention of the lacrimal implants. Depending on the purpose or use of the implant and the materials used for making the heel, the characteristics of the bore noted above are readily varied. Configurations of the bore 385 disclosed herein are illustrative and any other suitable configurations are within the scope of the present invention.

In FIG. 3F, an exemplary bore 385 is characterized by a third axis C and a second angle $\theta_2$ that is defined by the first axis with respect to the third axis A in a similar way as the first angle $\theta_1$. In some embodiments, the second angle $\theta_2$ is from about 15° to about 90°. For example, in some embodiments, the second angle $\theta_2$ is about 45°.

In some embodiments, the bore 385 has a depth along the direction of the third axis C that is from about 0.3 mm to about 0.7 mm. For example, in some embodiments the depth of the bore 385 is approximately 0.4 mm and in some embodiments is approximately 0.6 mm. The bore 385 may include a bore shaft 390 that is generally cylindrical, with a circular, elliptical, oval, or polygonal cross section. The bore 385 may further include a bore tip 395 at which the bore shaft 390 terminates. An exemplary bore tip 395 generally has a semispherical configuration. In some embodiments, the bore shaft 390 has a characteristic diameter that is from about 0.1 mm to about 0.3 mm. In some embodiments, the characteristic diameter of the bore is approximately 0.17 mm. As will be appreciated, the shapes, sizes, orientations disclosed in the present application are illustrative, and any other suitable shapes, sizes, or orientations are within the scope of the present application. In addition, it will be appreciated that the opening of the bore can be positioned closer to the second member or closer to the edge of the heel.

Figure 4A:
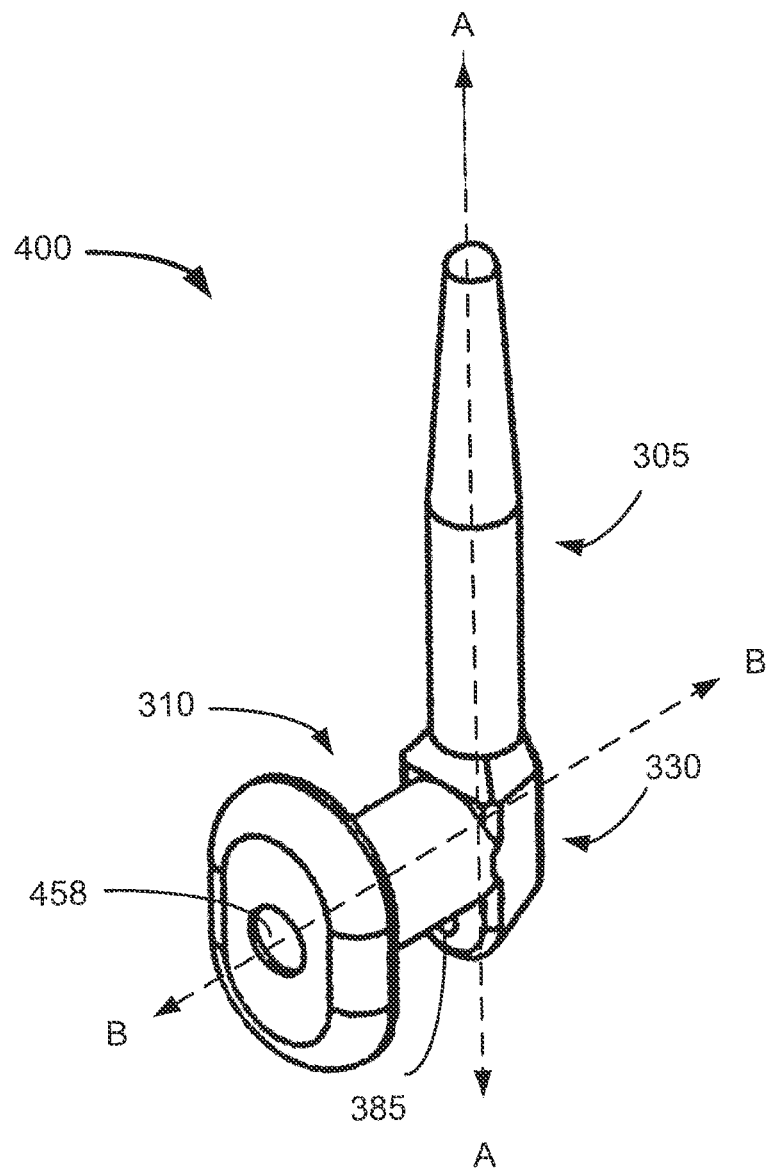
FIG. 4A provides a perspective view of an implant in accordance with an embodiment of the present invention.

FIG. 4A-4C illustrates an exemplary lacrimal implant 400 that is insertable through a lacrimal punctum 212, 214 and into its associated canaliculus 208, 210. In FIG. 4A, the lacrimal implant 400 comprises a cavity 458 that is configured to house a therapeutic agent core or other materials for release into an eye or surrounding tissues for treatment of various ocular, sinus or other diseases.

In the illustrated exemplary embodiment, the cavity 458 is formed in the head segment 340 and has an opening through the outer-surface 355. The cavity 458 can be shallow such that it stays within the head segment 340. The cavity 458 can be also deeper and extend beyond the head segment 340 and into the upright segment 335. Illustrated exemplary cavity 458 is in general substantially cylindrical with a circular cross section. Any other suitable configuration is within the scope of the present application. For example, in some embodiments, the cavity 458 has a truncated spherical configuration, or has a cylindrical configuration with an oblong or a polygonal cross section.

In some embodiments, the cavity 458 has a depth in the direction of the second axis B that is about from 0.2 mm to about 1.4 mm. For example, in some embodiments, the depth of the cavity 458 is approximately 1.2 mm. In some embodiments, the cavity 458 has a diameter that is from about 0.3 mm to about 0.7 mm. For example, in some embodiments the diameter of the cavity 458 is from about 0.42 mm to about 0.55 mm. In an exemplary embodiment, the cavity 458 extends into the upright segment 335, and the diameter of the cavity 458 is smaller than the diameter of the upright segment 335.

Referring to FIG. 4C, the cavity 458 includes a bottom 482. In various embodiments, the bottom 482 is rounded. In various embodiments, the rounded bottom has a radius of curvature that is from about 0.03 mm to about 0.07 mm.

Figure 5:
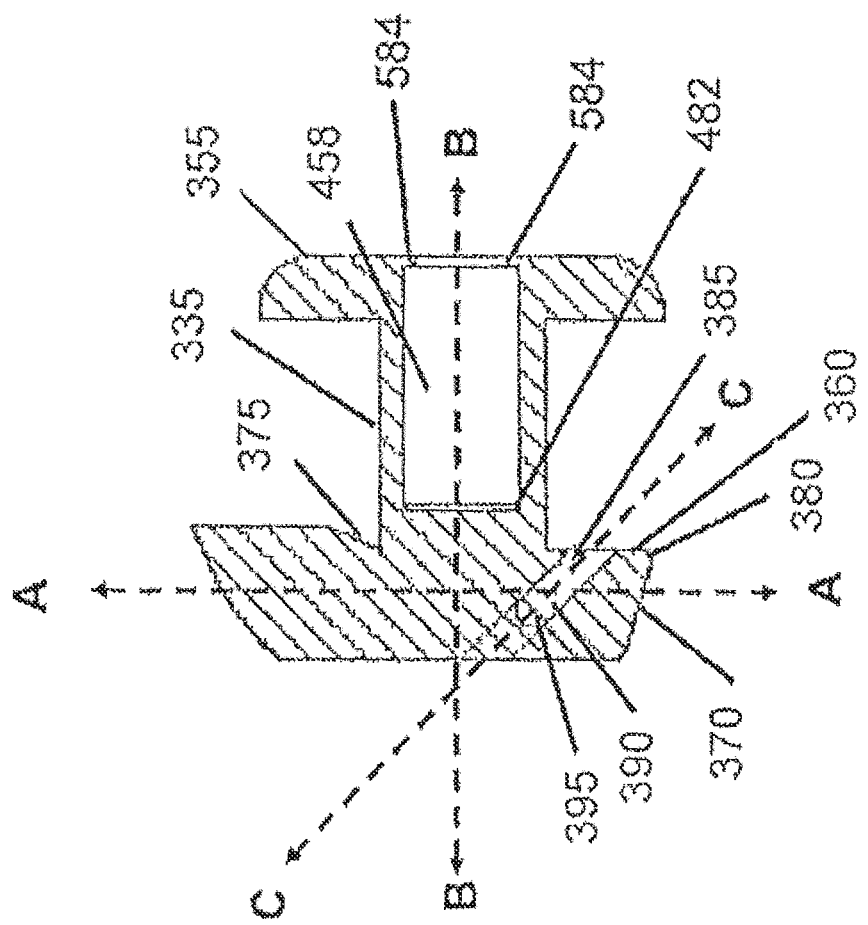
FIG. 5 provides a partial cross-sectional view of an implant in accordance with one embodiment of the present invention.
Figure 6:
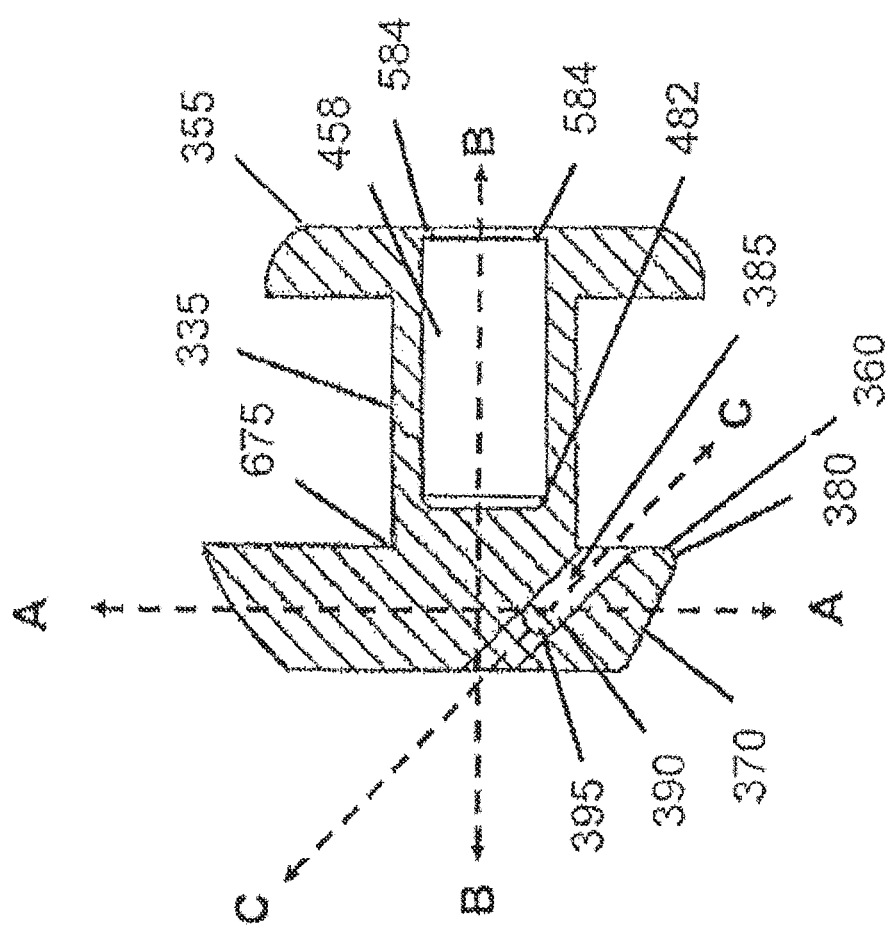
FIG. 6 provides a partial cross-section view of an implant in accordance with another embodiment of the present invention.

FIG. 5 depicts exemplary configurations of the cavity 458. In FIG. 5, the cavity 458 includes a lip 584 or other retaining structure positioned at the opening of the cavity 458. The lip 584 or the other retaining structure are optionally configured to partially enclose the cavity 458, e.g., prevent a therapeutic agent core or other materials from moving out of the cavity 458. In some embodiments, the lip 584 is a square cross sectional annulus that extends down from the outer-surface 355 into the cavity 458 and extends inwardly towards the center of the opening of the cavity 458. In some embodiments, the lip 584 is of a tab configuration and includes a plurality of spaced lips that extend inwardly into the opening of the cavity 458. The lip 584 may extend downwardly from about 0.02 mm to about 0.1 mm and inwardly from about 0.02 mm to about 0.1 mm. For example, in some embodiments, the lip 584 extends about 0.05 mm downwardly or inwardly.

Exemplary lacrimal implants of use in methods of the present invention are made of various materials including plastic, rubber, polymer, or composite. Exemplary lacrimal implants of the present invention formed from one or more material including plastic, rubber, polymer, composites, or other appropriate materials. In some embodiments, the lacrimal implants are formed from liquid silicone rubber. For instance, in exemplary embodiments, lacrimal implants are formed from a material marketed as NuSil 4840 liquid silicone rubber, NuSil 4870, or a mixture including such a liquid silicone rubber. Examples of such a mixture include a material marketed as 6-4800, which comprises NuSil 4840 with from about 1% to about 5%, e.g., from about 2% to about 4% 6-4800.

In some embodiments, the lacrimal implant is formed from biodegradable materials, for instance, biodegradable elastic materials including cross-linked polymers, such as poly (vinyl alcohol). In some embodiments, the lacrimal implant can comprise a co-polymer, such as silicone/polyurethane co-polymer, silicone/urethane, silicone/poly (ethylene glycol) (PEG), and silicone/2hydroxyethyl methacrylate (HEMA). As discussed in commonly-owned Utkhede et al., U.S. patent application Ser. No. 12/231,986, entitled "DRUG CORES FOR SUSTAINED RELEASE OF THERAPEUTIC AGENTS," filed Sep. 5, 2008, which is herein incorporated by reference in its entirety, urethane-based polymer and copolymer materials allow for a variety of processing methods and bond well to one another.

The hardness of the material is selected to facilitate or alter the retention of the lacrimal implant within the lacrimal punctum and its associated canaliculus. Accordingly, in some embodiments, a material having a durometer rating of from about 20D to about 80D, e.g., about 30D to about 70D, e.g., from about 40D to about 60D is of use to adjust parameters such as patient comfort and retention. For example, in some embodiments, the durometer rating of the material used to form the lacrimal implants is approximately 40D. Materials other than those exemplified above providing a durometer rating for the lacrimal implants within the stated ranges, and particularly that is about 40D are also of use. In some embodiments, a harder material or softer material is utilized for the entire lacrimal implant or for portions thereof. In such case, the lacrimal implants are formed from the materials that provide a durometer rating of about 70D.

In some embodiments, the lacrimal implants of use in the present methods are formed of multiple materials, where certain members or portions of the lacrimal implants are formed with materials having different properties. For example, in some embodiments the first member 305 is formed of a harder durometer rated material while the second member 310 is formed of a softer durometer rated material. In some embodiments, the first member 305 is formed of a softer durometer rated material while the second member 310 is formed of a harder durometer rated material.

In some embodiments the third member or heel 330 is formed of a harder durometer rated material than one or more parts of the remainder of the second member 310. In various embodiments, the third member or heel 330 is formed of a softer durometer rated material than the remainder of the second member 310.

Exemplary implants of use in the invention can be formed by methods known in the art, including, but not limited to, machining a blank to the desired shape and size and molding the material forming the implant.

The implant can be one of any number of different designs that releases anti-inflammatory agents and or drugs for a sustained period of time. The disclosures of the following patent documents, which disclose example implant structure or processing embodiments for use in the methods of embodiments of the current invention and methods of making those implants, are incorporated herein by reference in their entirety: U.S. Application Ser. No. 60/871,864 (filed Dec. 26, 2006 and entitled Nasolacrimal Drainage System Implants for Drug Therapy); U.S. application Ser. No. 11/695,537 (filed Apr. 2, 2007 and entitled Drug Delivery Methods, Structures, and Compositions for Nasolacrimal System); U.S. U.S. application Ser. No. 12/332,219 (filed Dec. 10, 2008 and entitled Drug Delivery Methods, Structures, and Compositions for Nasolacrimal System); U.S. Application Ser. No. 60/787,775 (filed Mar. 31, 2006 and entitled Nasolacrimal Drainage System Implants for Drug Therapy); U.S. application Ser. No. 11/695,545 (filed Apr. 2, 2007 and entitled Nasolacrimal Drainage System Implants for Drug Therapy); U.S. Application Ser. No. 60/585,287 (filed Jul. 2, 2004 and entitled Treatment Medium Delivery Device and Methods for Delivery of Such Treatment Mediums to the Eye Using Such a Delivery Device); U.S. application Ser. No. 11/571,147 (filed Dec. 21, 2006 and entitled Treatment Medium Delivery Device and Methods for Delivery of Such Treatment Mediums to the Eye Using Such a Delivery Device); U.S. Application Ser. No. 60/970,696 (filed Sep. 7, 2007 and entitled Expandable Nasolacrimal Drainage System Implants); U.S. Application Ser. No. 60/974,367 (filed Sep. 21, 2007 and entitled Expandable Nasolacrimal Drainage System Implants); U.S. Application Ser. No. 60/970,699 (filed Sep. 7, 2007 and entitled Manufacture of Drug Cores for Sustained Release of Therapeutic Agents); U.S. Application Ser. No. 60/970,709 (filed Sep. 7, 2007 and entitled Nasolacrimal Drainage System Implants for Drug Delivery); U.S. Application Ser. No. 60/970,720 (filed Sep. 7, 2007 and entitled Manufacture of Expandable Nasolacrimal Drainage System Implants); U.S. Application Ser. No. 60/970,755 (filed Sep. 7, 2007 and entitled Prostaglandin Analogues for Implant Devices and Methods); U.S. Application Ser. No. 60/970,820 (filed Sep. 7, 2007 and entitled Multiple Drug Delivery Systems and Combinations of Drugs with Punctal Implants); U.S. Application Ser. No. 61/066,223 (filed Feb. 18, 2008 and entitled Lacrimal Implants and Related Methods); U.S. Application Ser. No. 61/049,347 (filed Apr. 30, 2008 and entitled Lacrimal Implants and Related Methods); U.S. Application Ser. No. 61/033,211 (filed Mar. 3, 2008 and entitled Lacrimal Implants and Related Methods); U.S. Application Ser. No. 61/049,360 (filed Apr. 30, 2008 and entitled Lacrimal Implants and Related Methods); U.S. Application Ser. No. 61/052,595 (filed May 12, 2008 and entitled Lacrimal Implants and Related Methods); U.S. Application Ser. No. 61/075,309 (filed Jun. 24, 2008 and entitled Lacrimal Implants and Related Methods); U.S. Application Ser. No. 61/154,693 (filed Feb. 23, 2009 and entitled Lacrimal Implants and Related Methods); U.S. Application Ser. No. 61/209,036 (filed Mar. 2, 2009 and entitled Lacrimal Implants and Related Methods); U.S. Application Ser. No. 61/209,630 (filed Mar. 9, 2009 and entitled Lacrimal Implants and Related Methods); U.S. Application Ser. No. 61/036,816 (filed Mar. 14, 2008 and entitled Lacrimal Implants and Related Methods); U.S. Application Ser. No. 61/271,862 (filed Jul. 27, 2009 and entitled Lacrimal Implants and Related Methods); U.S. Application Ser. No. 61/252,057 (filed Oct. 15, 2009 and entitled Lacrimal Implants and Related Methods); U.S. application Ser. No. 12/710,855 (filed Feb. 23, 2010 and entitled Lacrimal Implants and Related Methods); U.S. Application Ser. No. 60/871,867 (filed Dec. 26, 2006 and entitled Drug Delivery Implants for Inhibition of Optical Defects); U.S. application Ser. No. 12/521,543 (filed Dec. 31, 2009 and entitled Drug Delivery Implants for Inhibition of Optical Defects); U.S. Application Ser. No. 61/052,068 (filed May 9, 2008 and entitled Sustained Release Delivery of Latanoprost to Treat Glaucoma); U.S. Application Ser. No. 61/052,113 (filed May 9, 2008 and entitled Sustained Release Delivery of Latanoprost to Treat Glaucoma); U.S. Application Ser. No. 61/108,777 (filed Oct. 27, 2008 and entitled Sustained Release Delivery of Latanoprost to Treat Glaucoma); U.S. application Ser. No. 12/463,279 (filed May 8, 2009 and entitled Sustained Release Delivery of Active Agents to Treat Glaucoma and Ocular Hypertension); U.S. Application Ser. No. 61/049,337 (filed Apr. 30, 2008 and entitled Lacrimal Implants and Related Methods); U.S. application Ser. No. 12/432,553 (filed Apr. 29, 2009 and entitled Composite Lacrimal Insert and Related Methods); U.S. Application Ser. No. 61/049,317 (filed Apr. 30, 2008 and entitled Drug-Releasing Polyurethane Lacrimal Insert); U.S. application Ser. No. 12/378,710 (filed Feb. 17, 2009 and entitled Lacrimal Implants and Related Methods); U.S. Application Ser. No. 61/075,284 (filed Jun. 24, 2008 and entitled Combination Treatment of Glaucoma); U.S. application Ser. No. 12/490,923 (filed Jun. 24, 2009 and entitled Combination Treatment of Glaucoma); U.S. Application Ser. No. 61/134,271 (filed Jul. 8, 2008 and entitled Lacrimal Implant Body Including Comforting Agent); U.S. application Ser. No. 12/499,605 (filed Jul. 8, 2009 and entitled Lacrimal Implant Body Including Comforting Agent); U.S. Application Ser. No. 61/057,246 (filed May 30, 2008 and entitled Surface Treatment of Implants and Related Methods); U.S. Application Ser. No. 61/132,927 (filed Jun. 24, 2008 and entitled Surface Treated Implantable Articles and Related Methods); U.S. application Ser. No. 12/283,002 (filed Sep. 5, 2008 and entitled Surface Treated Implantable Articles and Related Methods); U.S. application Ser. No. 12/231,989 (filed Sep. 5, 2008 and entitled Lacrimal Implants and Related Methods); U.S. Application Ser. No. 61/049,317 (filed Apr. 30, 2008 and entitled Drug-Releasing Polyurethane Lacrimal Insert); U.S. application Ser. No. 12/231,986 (filed Sep. 5, 2008 and entitled Drug Cores for Sustained Release of Therapeutic Agents); U.S. Application Ser. No. 61/050,901 (filed May 6, 2008 and entitled Punctum Plug Detection); U.S. application Ser. No. 12/231,987 (filed Sep. 5, 2008 and entitled Lacrimal Implant Detection); U.S. Application Ser. No. 61/146,860 (filed Jan. 23, 2009 and entitled Sustained Release Delivery of One or More Anti-Glaucoma Agents); U.S. Application Ser. No. 61/152,909 (filed Feb. 16, 2009 and entitled Sustained Release Delivery of One or More Anti-Glaucoma Agents); U.S. Application Ser. No. 61/228,894 (filed Jul. 27, 2009 and entitled Sustained Release Delivery of One or More Anti-Glaucoma Agents); U.S. Application Ser. No. 61/277,000 (filed Sep. 18, 2009 and entitled Drug Cores for Sustained Ocular Release of Therapeutic Agents); U.S. application Ser. No. 12/692,452 (filed Jan. 22, 2010 and entitled Sustained Release Delivery of One or More Agents); U.S. Application Ser. No. 61/283,100 (filed Nov. 27, 2009 and entitled Lacrimal Implants Including Split and Insertable Drug Core); International Application Serial No. PCT/US2010/058129 (filed Nov. 26, 2010, published as WO 2011/066479 and entitled Lacrimal Implants Including Split and Insertable Drug Core); U.S. Application Ser. No. 61/139,456 (filed Dec. 19, 2008 and entitled Substance Delivering Punctum Implants and Methods); U.S. application Ser. No. 12/643,502 (filed Dec. 21, 2009 and entitled Substance Delivering Punctum Implants and Methods); U.S. application Ser. No. 10/825,047 (filed Apr. 15, 2004 and entitled Drug Delivery via Punctal Plug); U.S. application Ser. No. 12/604,202 (filed Oct. 22, 2009 and entitled Drug Delivery via Ocular Implant); International Application Serial No. PCT/US2005/023848 (filed Jul. 1, 2005, published as WO 2006/014434 and entitled Treatment Medium Delivery Device and Methods for Delivery); International Application Serial No. PCT/US2007/065792 (filed Apr. 2, 2007, published as WO 2007/115261 and entitled Drug Delivery Methods, Structures, and Compositions for Nasolacrimal System); and International Application Serial No. PCT/US2007/065789 (filed Apr. 2, 2007, published as WO 2007/115259 and entitled Nasolacrimal Drainage System Implants for Drug Therapy).

In various embodiments of the methods of the invention, an implant including a retention structure is employed to retain the implant in the punctum or canaliculus. The retention structure is attached to or integral with the implant body. The retention structure comprises an appropriate material that is sized and shaped so that the implant can be easily positioned in the desired tissue location, for example, the punctum or canaliculus. In some embodiments, the drug core may be attached to the retention structure via, at least in part, the sheath. In some embodiments, the retention structure comprises a hydrogel configured to expand when the retention structure is placed in the punctum. The retention structure can comprise an attachment member having an axially oriented surface. In some embodiments, expansion of the hydrogel can urge against the axially oriented surface to retain the hydrogel while the hydrogel is hydrated. In some embodiments, the attachment member can comprise at least one of a protrusion, a flange, a rim, or an opening through a portion of the retention structure. In some embodiments, the retention structure includes an implant body portion size and shape to substantially match an anatomy of the punctum and canaliculus.

The retention structure may have a size suitable to fit at least partially within the canalicular lumen. The retention structure can be expandable between a small profile configuration suitable for insertion and a large profile configuration to anchor the retention structure in the lumen, and the retention structure can be attached near the distal end of the drug core. In specific embodiments, the retention structure can slide along the drug core near the proximal end when the retention structure expands from the small profile configuration to the large profile configuration. A length of the retention structure along the drug core can be shorter in the large profile configuration than the small profile configuration.

In some embodiments, the retention structure is resiliently expandable. The small profile may have a cross section of no more than about 0.2 mm, and the large profile may have a cross section of no more than about 2.0 mm. The retention structure may comprise a tubular body having arms separated by slots. The retention structure can be disposed at least partially over the drug core.

In some embodiments, the retention structure is mechanically deployable and typically expands to a desired cross sectional shape, for example with the retention structure comprising a super elastic shape memory alloy such as Nitinol™. Other materials in addition to Nitinol™ can be used, for example resilient metals or polymers, plastically deformable metals or polymers, shape memory polymers, and the like, to provide the desired expansion. In some embodiments polymers and coated fibers available from Biogeneral, Inc. of San Diego, CA may be used. Many metals such as stainless steels and non-shape memory alloys can be used and provide the desired expansion. This expansion capability permits the implant to fit in hollow tissue structures of varying sizes, for example canaliculae ranging from 0.3 mm to 1.2 mm (i.e. one size fits all). Although a single retention structure can be made to fit canaliculae from 0.3 to 1.2 mm across, a plurality of alternatively selectable retention structures can be used to fit this range if desired, for example a first retention structure for canaliculae from 0.3 to about 0.9 mm and a second retention structure for canaliculae from about 0.9 to 1.2 mm. The retention structure has a length appropriate to the anatomical structure to which the retention structure attaches, for example a length of about 3 mm for a retention structure positioned near the punctum of the canaliculus. For different anatomical structures, the length can be appropriate to provide adequate retention force, e.g. 1 mm to 15 mm lengths as appropriate.

Although the implant body may be attached to one end of the retention structure as described above, in many embodiments the other end of the retention structure is not attached to the implant body so that the retention structure can slide over the implant body including the sheath body and drug core while the retention structure expands. This sliding capability on one end is desirable as the retention structure may shrink in length as the retention structure expands in width to assume the desired cross sectional width. However, it should be noted that many embodiments may employ a sheath body that does not slide in relative to the core.

In many embodiments, the retention structure can be retrieved from tissue. A projection, for example a hook, a loop, or a ring, can extend from a portion of the implant body to facilitate removal of the retention structure.

In some embodiments the sheath and retention structure can comprise two parts.

The lacrimal implants of the present invention have exceptional retention properties, and are retained in the punctum and canaliculus for a period that is enhanced relative to a commercially available plug based upon the percentage of eyes in which an implant was implanted retaining the implant over a selected time period.

In an exemplary embodiment, the method of the invention uses a lacrimal implant configured to remain implanted in a punctum for at least about 1 week, 2 weeks, 3 weeks, 4 weeks, 5 weeks, 6 weeks, 7 weeks, 8, weeks, 9 weeks 10 weeks, 11 weeks, or at least about 12 weeks or more. In an exemplary embodiment, the lacrimal implant is configured to be retained by the puncta for the duration of the intended sustained release of the therapeutic agent. In various embodiments, the duration of the intended sustained release of the therapeutic agent is at least about 1 week, 2 weeks, 3 weeks, 4 weeks, 5 weeks, 6 weeks, 7 weeks, 8, weeks, 9 weeks 10 weeks, 11 weeks, or at least about 12 weeks or more. In various embodiments at least about 95%, at least about 90%, at least about 85% or at least about 80% of the implanted implants are retained for the duration of the intended controlled release of the therapeutic agent. In an exemplary embodiment, the implant is retained by the puncta for a length of time to show therapeutic efficacy.

In various embodiments, the present invention provides for the use of implants having structural features that enhance the retention of the implant in a puncta. Amongst other features, the heel of the present implant (e.g., 330) is configured to come to rest in the lacrimal canaliculus ampulla (e.g., 252), effectively locking the implant into place. However, the inventors have recognized that to prevent rotation and relative movement of the implanted device, which plays a role in the displacement of the device, a first member was needed to maintain the heel in the ampulla. Thus, the first member, e.g., 305, is configured to stabilize the punctal plug within the lacrimal canaliculus, prevent rotation and maintain positioning of the plug when the surrounding tissue moves.

In an exemplary embodiment, the methods of the invention use an implant having an occlusive element. An occlusive element can be mounted to and expandable with the retention structure to inhibit tear flow. An occlusive element may inhibit tear flow through the lumen, and the occlusive element may cover at least a portion of the retention structure to protect the lumen from the retention structure. The occlusive element comprises an appropriate material that is sized and shaped so that the implant can at least partially inhibit, even block, the flow of fluid through the hollow tissue structure, for example lacrimal fluid through the canaliculus. The occlusive material may be a thin walled membrane of a biocompatible material, for example silicone, that can expand and contract with the retention structure. The occlusive element is formed as a separate thin tube of material that is slid over the end of the retention structure and anchored to one end of the retention structure as described above. Alternatively, the occlusive element can be formed by dip coating the retention structure in a biocompatible polymer, for example silicone polymer. The thickness of the occlusive element can be in a range from about 0.01 mm to about 0.15 mm, and often from about 0.05 mm to 0.1 mm.

Methods of Use

In embodiments, provided herein are methods for delivering an ophthalmic drug to an eye for pre- or post-cataract surgery treatment, comprising: placing a medical device disclosed herein comprising any one of the solid matrix sustained release ophthalmic formulations disclosed herein, on, in or near the eye of a patient, wherein the ophthalmic drug is a NSAID or steroidal anti-inflammatory drug. In certain embodiments, the medical device is a lacrimal implant, wherein the lacrimal implant is placed through a punctum and into a canalicular lumen of a patient. In certain other embodiments, the medical device is an intracanalicular plug, wherein the intracanalicular plug is placed through a punctum and into a canalicular lumen of a patient. In other embodiments, the medical device is an ocular ring, wherein the ring is placed on the surface of the eye and under the eye lid (outside the field of vision).

In embodiments, treatment period for pre- or post-cataract surgery is about 2 weeks to about 4 weeks.

In embodiments, provided herein are methods for delivering an ophthalmic drug to an eye for dry-eye treatment, comprising: placing a medical device disclosed herein comprising any one of the solid matrix sustained release ophthalmic formulations disclosed herein, on, in or near the eye of a patient, wherein the ophthalmic drug cyclosporine. In certain embodiments, the medical device is a lacrimal implant, wherein the lacrimal implant is placed through a punctum and into a canalicular lumen of a patient. In certain other embodiments, the medical device is an intracanalicular plug, wherein the intracanalicular plug is placed through a punctum and into a canalicular lumen of a patient. In other embodiments, the medical device is an ocular ring, wherein the ring is placed on the surface of the eye and under the eye lid (outside the field of vision).

In embodiments, treatment period for dry eye is about one month to about 6 months.

The methods of the present invention can be administered to a mammal in need of treatment by way of a variety of routes. For example, drug delivery systems may be used by implantation within a portion of the body in need of localized drug delivery, e.g., the interior portion of an eye. However, the exemplary matrix controlled diffusion drug delivery systems may likewise be used in accordance with other surgical procedures known to those skilled in the field of ophthalmology. For example, the drug delivery systems can be administered to the region of the eye in need of treatment employing instruments known in the art, e.g., a flexible microcatheter system or cannula disclosed in U.S. Patent Application Publication No. 2002/0002362, or the intraretinal delivery and withdrawal systems disclosed in U.S. Pat. Nos. 5,273,530 and 5,409,457, the contents of each which are incorporated by reference herein. The pharmaceutically active agent may be released from the drug delivery device over a sustained and extended period of time. Optionally, the drug release rate may also be controlled through the attachment of an inert diffusion barrier by way of, for example, surface treatment of the drug delivery device. The surface treatment may be applied through a variety of surface treatment techniques known in the art, e.g., oxidative plasma, evaporative deposition, dip coating or extrusion techniques.

Optional Formulation Components

The present formulation may further comprise a pharmaceutically acceptable carrier, e.g., excipients, suspending agents, diluents, fillers, salts, buffers, stabilizers, solubilizers, solvents, dispersion media, coatings, isotonic agents, and other materials known in the art. The pharmaceutical formulation optionally includes potentiators, complexing agents, targeting agents, stabilizing agents, cosolvents, pressurized gases, or solubilizing conjugates.

Exemplary excipients include sugars such as lactose, sucrose, mannitol, or sorbitol; cellulose preparations such as, maize starch, wheat starch, rice starch, potato starch, gelatin, gum tragacanth, methyl cellulose, hydroxypropylmethylcellulose, sodium caroxymethylcellulose, and/or polyvinylpyrrolidone (PVP). Preferred excipients include lactose, gelatin, sodium carboxymethyl cellulose, and low molecular weight starch products.

Exemplary suspending agents that can serve as valve lubricants in pressurized pack inhaler systems are desirable. Such agents include oleic acid, simple carboxylic acid derivatives, and sorbitan trioleate.

Exemplary diluents include water, saline, phosphate-buffered citrate or saline solution, and mucolytic preparations. Other diluents that can be considered include alcohol, propylene glycol, and ethanol; these solvents or diluents are more common in oral aerosol formulations. Physiologically acceptable diluents that have a tonicity and pH compatible with the alveolar apparatus are desirable. Preferred diluents include isotonic saline, phosphate buffered isotonic solutions whose tonicity have been adjusted with sodium chloride or sucrose or dextrose or mannitol.

Exemplary fillers include glycerin, propylene glycol, ethanol in liquid or fluid preparations. Suitable fillers for dry powder inhalation systems include lactose, sucrose, dextrose, suitable amino acids, and derivatives of lactose. Preferred fillers include glycerin, propylene glycol, lactose and certain amino acids.

Exemplary salts include those that are physiologically compatible and provide the desired tonicity adjustment. Monovalent and divalent salts of strong or weak acids are desirable. Preferred salts include sodium chloride, sodium citrate, ascorbates, sodium phosphates.

Exemplary buffers include phosphate or citrate buffers or mixed buffer systems of low buffering capacity. Preferred buffers include phosphate or citrate buffers.

EXAMPLES

The following examples are put forth so as to provide those of ordinary skill in the art with a complete disclosure and description of how to use the embodiments provided herein, and are not intended to limit the scope of the disclosure nor are they intended to represent that the Examples below are all of the experiments or the only experiments performed. Efforts have been made to ensure accuracy with respect to numbers used (e.g. amounts, temperature, etc.) but some experimental errors and deviations should be accounted for. Unless indicated otherwise, parts are parts by volume, and temperature is in degrees Centigrade. It should be understood that variations in the methods as described can be made without changing the fundamental aspects that the Examples are meant to illustrate.

Example 1: Manufacturing of Nepafenac Drug Inserts in a Polycaprolactone and PEG400 Matrix Nepafenac (0.685 g), polycaprolactone polymers (0.210 g; SigmaAldrich) and polyethylene glycol 400 (PEG 400) (0.105 g; SigmaAldrich) were dissolved in 70 ml of tetrahydrofuran (THF) by shaking at room temperature until a translucent yellow solution was achieved; mixing time was about 2.5 hours. The mixture was dried down using a rotary evaporator to remove the THF and vacuum oven at 40° C. followed by a high vacuum for at least 12 hours. Next the dried mixture was transferred to a glass slide and melted on a hot plate with manual mixing; the mixture was then allowed to cool. The cooled mixture was transferred to a stainless steel syringe attached to a 12 inch long polyimide sheath (inner diameter of 0.022 inches and an outer diameter of 0.024 inches), wherein the mixture was extruded into the sheath in a heated (70° C.) extruder under pressure (60 psi). The extruded nepafenac/polycaprolactone/PEG400 mixture was allowed to cool and the sheath cut into 0.95 mm lengths, wherein one end was sealed with a cyanoacrylate adhesive. The completed Nepafenac drug inserts were then placed in the receiving cavity of a punctal plug, which are disclosed herein. Each drug insert contained about 192±14 μg of Nepafenac.

Example 2: Manufacturing of Nepafenac Drug Inserts in a Polycaprolactone and PEG400 Matrix with Surfactant Nepafenac (1.32 g), polycaprolactone polymers (0.400 g; SigmaAldrich), polyethylene glycol 400 (PEG 400) (0.200 g; SigmaAldrich) and tyloxapol (0.080 g; SigmaAldrich) were dissolved in 100 ml of tetrahydrofuran (THF) by shaking at 60° C. until a clear yellow solution was achieved; mixing time was about 10 minutes. The mixture was dried down using a rotary evaporator to remove the THF and vacuum oven at 60° C. followed by a high vacuum for at least 12 hours. Next the dried mixture was mixed in the round bottom flask using a heating mantle with manual mixing; the mixture was then allowed to cool. The cooled mixture was transferred to a stainless steel syringe attached to a 12 inch long polyimide sheath (inner diameter of 0.022 inches and an outer diameter of 0.024 inches), wherein the mixture was extruded into the sheath in a heated (62° C.) extruder under pressure (30 psi). The extruded nepafenac/polycaprolactone/PEG400/tyloxapol mixture was allowed to cool and the sheath cut into 0.95 mm lengths, wherein one end was sealed with a cyanoacrylate adhesive. The completed Nepafenac drug inserts were then placed in the receiving cavity of a punctal plug, which are disclosed herein. Each drug insert contained about 204 μg of Nepafenac.

Example 3: Elution Profile of Nepafenac Drug Insert in a Polycaprolactone and PEG400 Matrix (with and without Surfactant)

Figure 7:
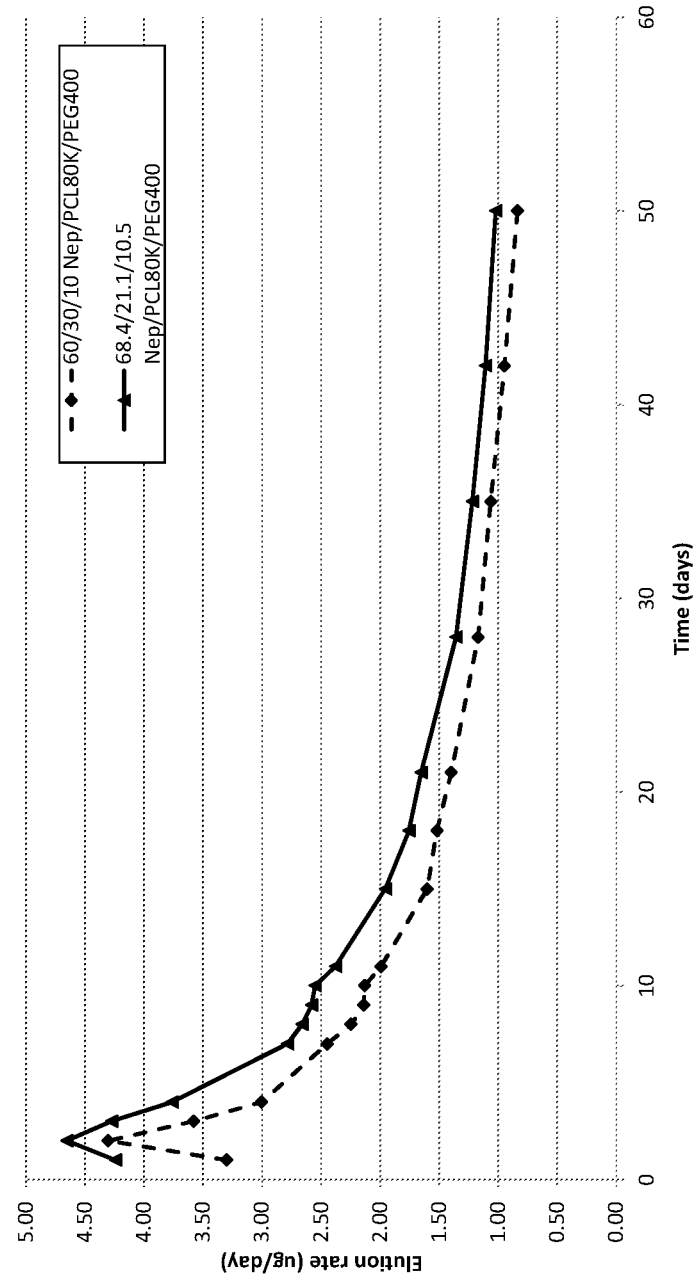
FIG. 7 provides an elution profile for a drug insert comprising nepafenac in a matrix comprising polycaprolactone and PEG polymers.

The Nepafenac drug inserts were prepared as disclosed in Example 1. Each drug insert comprises a range of 60-70% w/w for Nepafenac; 30-21% w/w for polycaprolactone 80K polymers; and, 10 to 10.5% w/w for PEG 400 polymers. Elution of Nepafenac from the drug inserts was evaluated by placing the drug insert (in the punctal plug) in about 1 ml of elution buffer (Phosphate buffered saline with 0.1% SDS (sodium dodecyl sulphate)). The punctal plug comprising the Nepafenac drug insert was transferred to new elution buffer daily and the amount of drug in the buffer measured. The results demonstrate a prolonged elution of Nepafenac of at least 1 μg per day over a period of 50 days. See FIG. 7.

Figure 8:
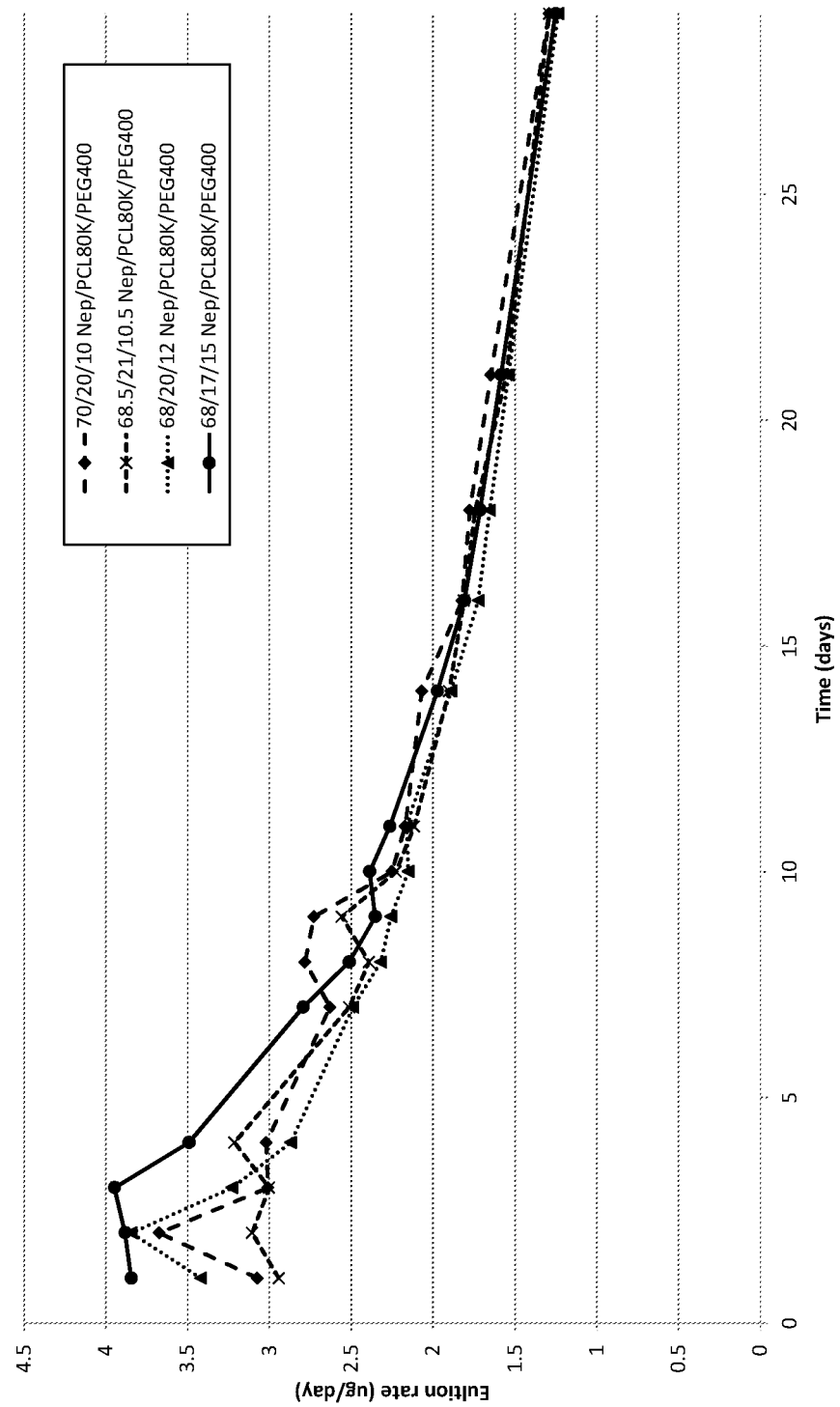
FIG. 8 provides an elution profile for a drug insert comprising nepafenac in a matrix comprising polycaprolactone and PEG polymers.

Further elution studies were performed wherein the drug inserts were prepared essentially as disclosed in Example 1 where each drug insert comprised a range of 50-70% w/w for Nepafenac; 17-21% w/w for polycaprolactone polymers; and, 10-15% w/w for PEG 400 polymers. Elution of Nepafenac from the drug inserts was evaluated essentially as disclosed above. The results demonstrate a prolonged elution of Nepafenac of at least 1 μg per day over a period of 30 days. See FIG. 8.

Figure 14:
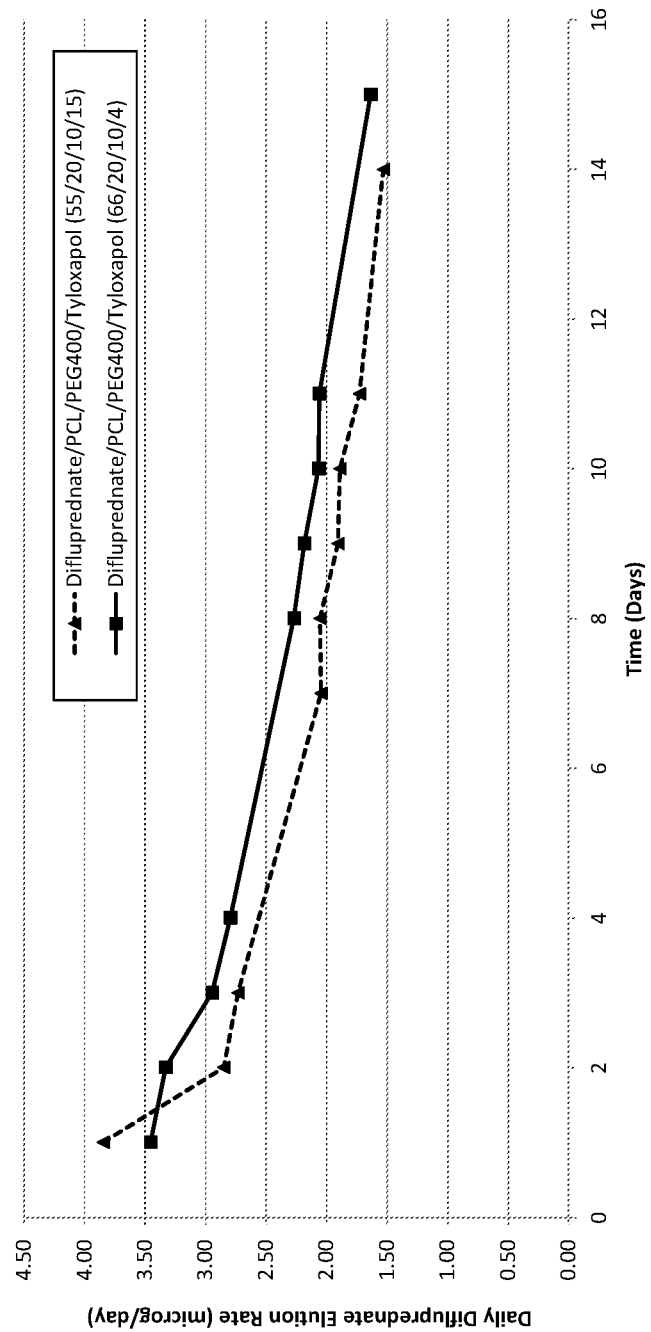
FIG. 14 provides an elution profile of a drug insert comprising difluprednate in a matrix comprising PEG 400 polymers, polycaprolactone and tyloxapol.

Further elution studies were performed wherein the drug inserts were prepared essentially as disclosed in Example 2 where each drug insert comprised a range of 55-66% w/w for Nepafenac; 20% w/w for polycaprolactone polymers; 4-15% w/w surfactant (tyloxapol or polysorbate 80); and, 10% w/w for PEG 400 polymers. Elution of Nepafenac from the drug inserts was evaluated essentially as disclosed above. The results demonstrate a prolonged elution of Nepafenac of at least 1.5 μg per day over a period of 14 days. The addition of surfactant improved the efficiency of the extrusion of the solid matrix. See FIG. 14.

A final elution study was performed wherein the drug inserts were prepared essentially as disclosed in Example 2 where each drug insert comprised about 66% w/w for Nepafenac; about 20% w/w for polycaprolactone polymers; about 10% w/w for PEG 400 polymers and about 4% w/w for tyloxapol. Elution of Nepafenac from the drug inserts was evaluated essentially as disclosed above. The results demonstrate a prolonged elution of Nepafenac of at least 1 μg per day over a period of 15 days. See FIG. 10

Example 4: Manufacturing of Difluprednate in a PEG400 Matrix

Difluprednate (0.240 g) and polyethylene glycol 400 (PEG 400) (0.060 g; SigmaAldrich) were dissolved in about 15 ml of chloroform by shaking at room temperature until a clear colorless solution was achieved. The mixture was dried down using a rotary evaporator to remove the solvent and vacuum oven at 40° C. for at least 12 hours. The dried mixture was transferred to a stainless steel syringe attached to a 12 inch long polyimide sheath (inner diameter of 0.022 inches and an outer diameter of 0.024 inches), wherein the mixture was extruded into the sheath in a heated (240° C.) extruder under pressure (up to 45 psi). The extruded difluprednate/PEG400 mixture was allowed to cool and the sheath cut into 0.95 mm lengths, wherein one end was sealed with a cyanoacrylate adhesive. The completed Difluprednate drug inserts were then placed in the receiving cavity of a punctal plug, which are disclosed herein. Each drug insert contained about 193±11 µg of Difluprednate.

Example 5: Elution Profile of Difluprednate Drug Insert in a PEG400 Matrix

Figure 9:
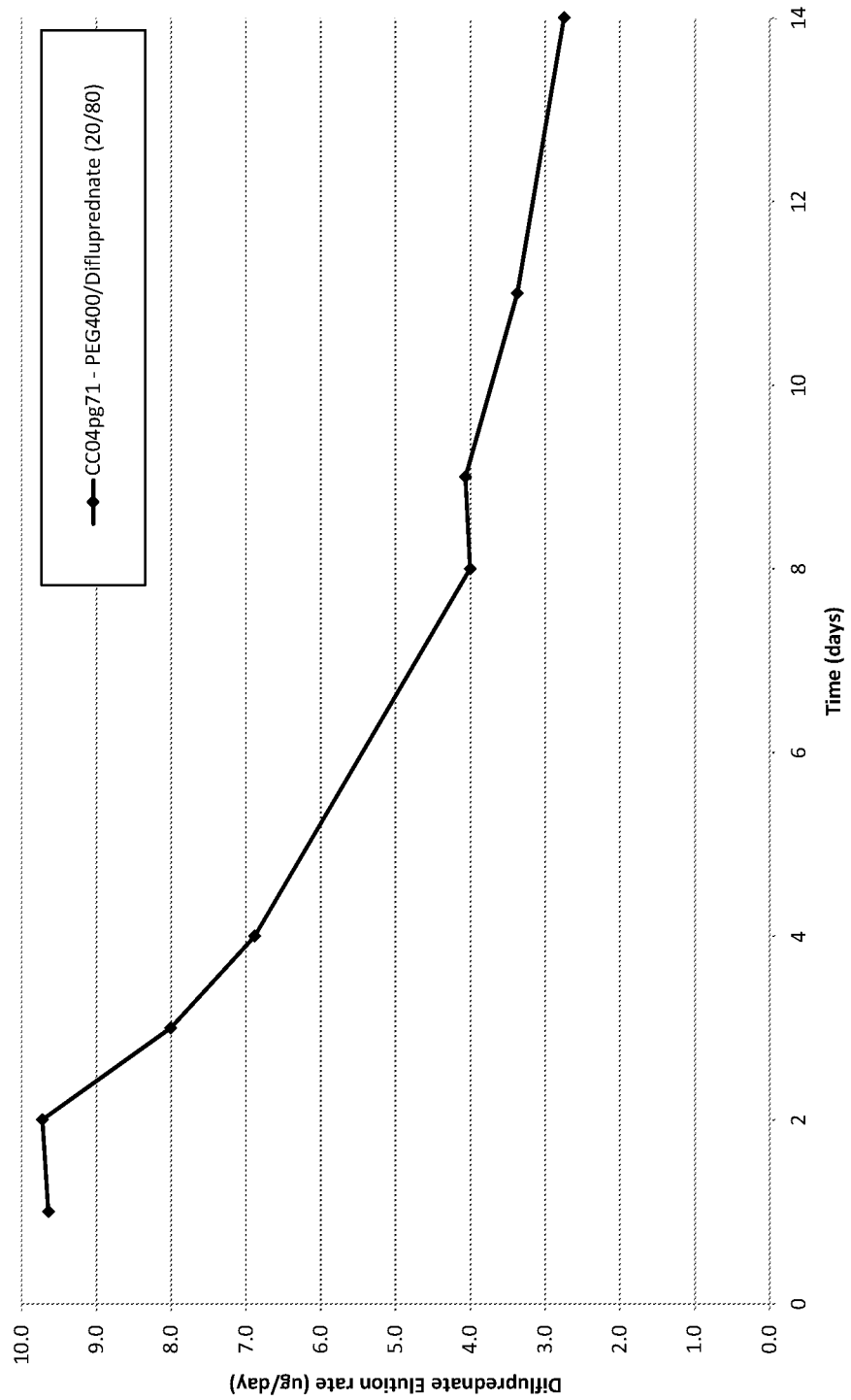
FIG. 9 provides an elution profile for a drug insert comprising difluprednate in a matrix comprising PEG polymers.

The Difluprednate drug inserts were prepared as disclosed in Example 4. Each drug insert comprises about 80% w/w of Difluprednate and about 20% w/w of PEG 400 polymers. Elution of Difluprednate from the drug inserts was evaluated by placing the drug insert (in the punctal plug) in about 1 ml of elution buffer (Phosphate buffered saline with 0.1% SDS (sodium dodecyl sulphate)). The punctal plug comprising the Difluprednate drug insert was transferred to new elution buffer daily and the amount of drug in the buffer measured. The results demonstrate a prolonged elution of Difluprednate of at least 2 µg per day over a period of 14 days. See FIG. 9.

Example 6: Manufacturing of Difluprednate in a PEG2000 Matrix with Surfactant

Difluprednate (0.240 g), polysorbate 80 (0.020 g) and polyethylene glycol 2000 (PEG 2000) (0.060 g; SigmaAldrich) were dissolved in about 15 ml of dichloromethane by shaking at room temperature until a clear colorless solution was achieved. The mixture was dried down using a rotary evaporator to remove the solvent and vacuum oven at approximately 40° C. for at least 12 hours. The dried mixture was transferred to a stainless steel syringe attached to a 12 inch long polyimide sheath (inner diameter of 0.022 inches and an outer diameter of 0.024 inches), wherein the mixture was extruded into the sheath in a heated (200° C.) extruder under pressure (up to 45 psi). The extruded difluprednate/PEG2000/polysorbate 80 mixture was allowed to cool and the sheath cut into 0.95 mm lengths, wherein one end was sealed with a cyanoacrylate adhesive. The completed Difluprednate drug inserts were then placed in the receiving cavity of a punctal plug, which are disclosed herein. Each drug insert contained about 110 µg of Difluprednate.

Figure 11:
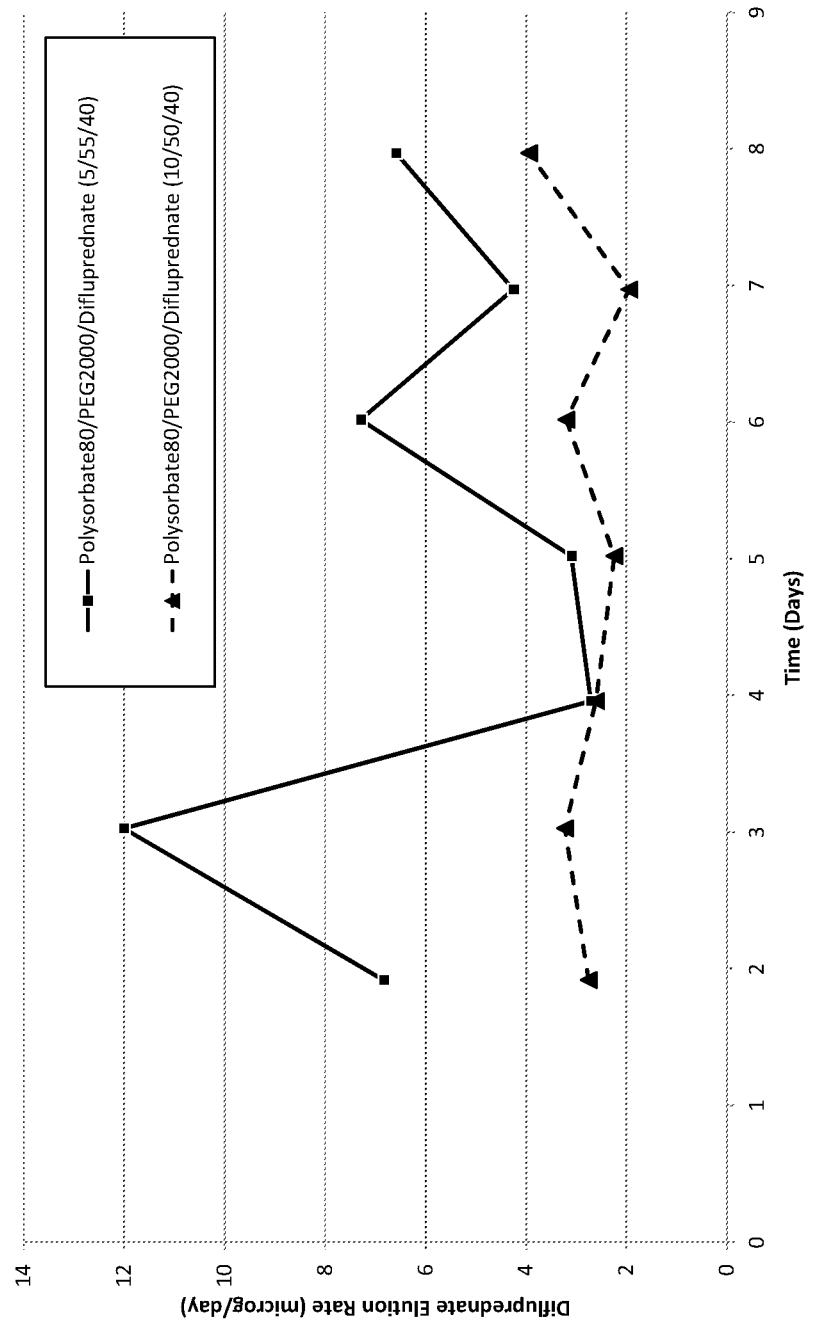
FIG. 11 provides an elution profile of a drug insert comprising difluprednate in a matrix comprising PEG 2000 polymers and polysorbate 80.

Example 7: Elution Profile of Difluprednate Drug Insert in a PEG2000 Matrix with Surfactant The Difluprednate drug inserts were prepared as disclosed in Example 6. Each drug insert comprises about 40% w/w of Difluprednate, 5-10% of polysorbate 80 and about 45-50% w/w of PEG 2000 polymers. Elution of Difluprednate from the drug inserts was evaluated by placing the drug insert (in the punctal plug) in about 1 ml of elution buffer (Phosphate buffered saline with 0.1% SDS (sodium dodecyl sulphate)). The punctal plug comprising the Difluprednate drug insert was transferred to new elution buffer daily and the amount of drug in the buffer measured. The results demonstrate a prolonged elution of Difluprednate of at least 2 µg per day over a period of 8 days. See FIG. 11.

Example 8: Manufacturing of Difluprednate Drug Insert in a Combination of a Solid and Liquid Surfactant Difluprednate (0.120 g), polysorbate 80 (0.045 g) and Sorbitan monopalmitate (Span 40) were dissolved in about 15 ml of dichloromethane by shaking at room temperature until a clear colorless solution is achieved. The mixture was dried down using a rotary evaporator to remove the solvent and vacuum oven at approximately 40° C. for at least 12 hours. The dried mixture was transferred to a stainless steel syringe attached to a 12 inch long polyimide sheath (inner diameter of 0.022 inches and an outer diameter of 0.024 inches), wherein the mixture was extruded into the sheath in a heated (200° C.) extruder under pressure (up to 45 psi). The extruded difluprednate/polysorbate 80/Span 40 mixture was allowed to cool and the sheath cut into 0.95 mm lengths, wherein one end is sealed with a cyanoacrylate adhesive. The completed Difluprednate drug inserts were then placed in the receiving cavity of a punctal plug, which are disclosed herein. Each drug insert contained about 110 µg of Difluprednate.

Figure 15:
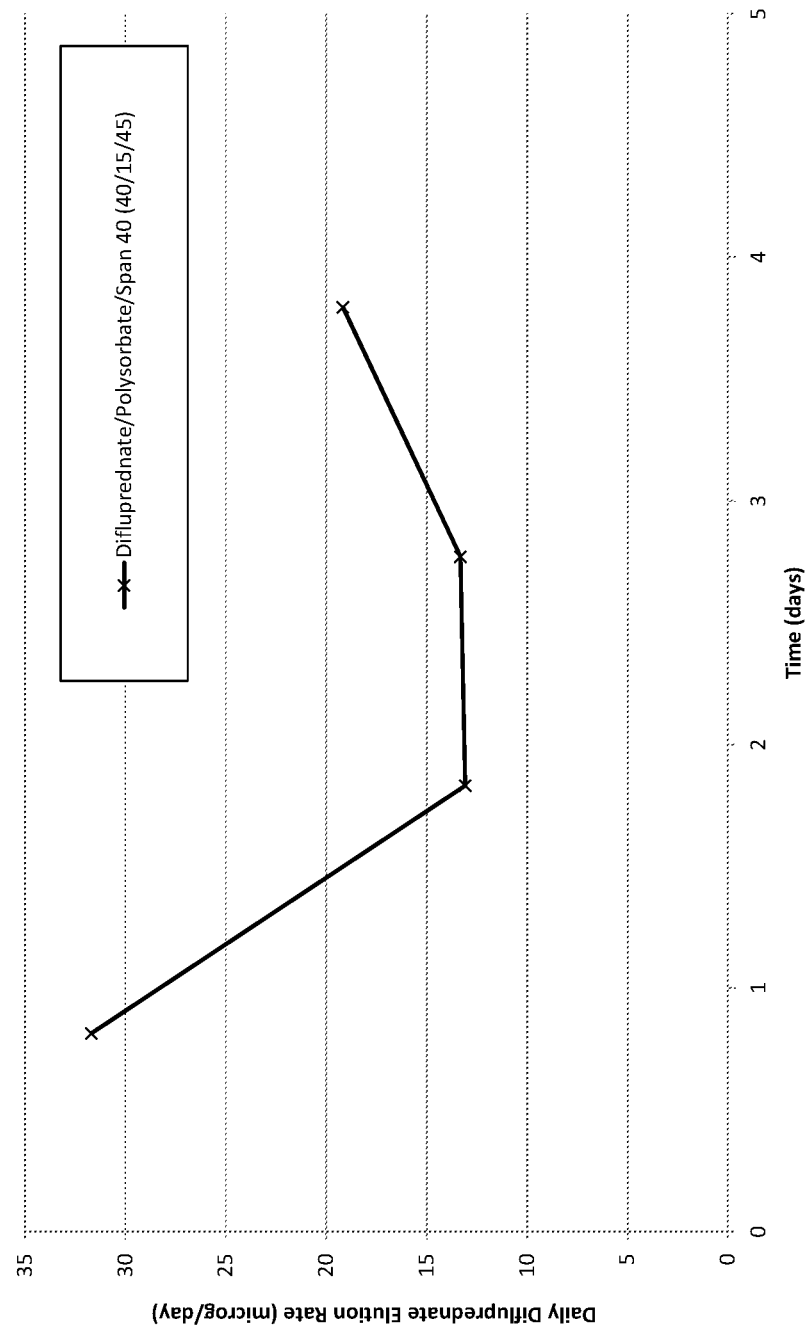
FIG. 15 provides an elution profile of a drug insert comprising difluprednate in a matrix comprising polysorbate 80 and Span 40 (Sorbitan monopalmitate).

Example 9: Elution Profile of Difluprednate Drug Insert in a Matrix with a Combination of Solid and Liquid Surfactant The Difluprednate drug inserts are prepared as disclosed in Example 8. Each drug insert comprises about 40-60% (w/w) of Difluprednate, 10-15% w/w of polysorbate 80 and about 30-45% w/w of Span 40. Elution of Difluprednate from the drug inserts is evaluated by placing the drug insert (in the punctal plug) in about 1 ml of elution buffer (Phosphate buffered saline with 0.1% SDS (sodium dodecyl sulphate)). The punctal plug comprising the Difluprednate drug insert are transferred to new elution buffer daily and the amount of drug in the buffer measured. The results demonstrate a prolonged elution of Difluprednate of at least 10 µg per day over a period of 4 days for a formulation of 40% (w/w) of Difluprednate, 15% of polysorbate 80 and about 45% w/w of Span 40. See FIG. 15.

Example 10: Manufacturing of Cyclosporine Drug Insert in a Polycaprolactone and PEG 2000 Matrix with Surfactant Cyclosporine A (0.292 g), polysorbate 80 (0.146 g), polycaprolactone (0.013 g) and polyethylene glycol 2000 (PEG 2000) (0.049 g; SigmaAldrich) were dissolved in about 10 ml of tetrahydrofuran by stirring at room temperature until a clear colorless solution was achieved. The mixture was dried down using a rotary evaporator to remove the solvent and vacuum oven at 50° C. for at least 12 hours. The dried mixture was transferred to a stainless steel syringe attached to a 12 inch long polyimide sheath (inner diameter of 0.022 inches and an outer diameter of 0.024 inches), wherein the mixture was extruded into the sheath in a heated (approximately 75° C.) extruder under pressure (up to 10 psi). The extruded cyclosporine A/PEG2000/polysorbate 80/polycaprolactone mixture was allowed to cool and the sheath cut into 0.95 mm lengths, wherein one end was sealed with a cyanoacrylate adhesive. The completed Cyclosporine A drug inserts were then placed in the receiving cavity of a punctal plug, which are disclosed herein. Each drug insert contained about 150±2 μg of Cyclosporine.

Example 11: Elution Profile of Cyclosporine a Drug Insert in a Polycaprolactone and PEG 2000 Matrix with Surfactant The Cyclosporine A drug inserts were prepared as disclosed in Example 9. Each drug insert comprises about 36-58.5% w/w of Cyclosporine A, 18-29.25% w/w of polysorbate 80, 2.5-40% w/w of polycaprolactone and about 6-9.75% w/w of PEG 2000 polymers. Elution of Cyclosporine A from the drug inserts was evaluated by placing the drug insert (in the punctal plug) in about 1 ml of elution buffer (Phosphate buffered saline with 0.1% SDS (sodium dodecyl sulphate)). The punctal plug comprising the Cyclosporine A drug insert was transferred to new elution buffer daily and the amount of drug in the buffer measured. The results demonstrate a prolonged elution of Cyclosporine of at least 2 μg per day over a period of 28 days. See FIGS. 12 and 13.

The invention claimed is:

1. A drug insert for topical delivery of nepafenac, comprising
a solid matrix, comprising about 30 to about 15% (w/w) of polycaprolactone, about 5 to about 15% (w/w) of polyethylene glycol (PEG) polymers, about 1 to about 15% w/w of tyloxapol and about 60 to about 70% (w/w) of nepafenac.

2. The drug insert of claim 1, wherein the polycaprolactone is present from about 17 to 21% (w/w), the PEG polymers are present from about 10 to 15%, the tyloxapol is present from about 1 to 10% (w/w) and the nepafenac is present from about 68 to 70% (w/w).

3. The drug insert of claim 1, wherein the PEG polymer is PEG 400.

4. The drug insert of claim 3, wherein the PEG 400 is present at about 10% (w/w).

5. The drug insert of claim 1, wherein the nepafenac is present at about 66% (w/w).

6. The drug insert of claim 1, wherein the tyloxapol is present at about 4% (w/w).

7. The drug insert of claim 1, wherein the polycaprolactone is present at about 20% (w/w).

8. The drug insert of claim 1, comprising: about 20% (w/w) of polycaprolactone, about 10% (w/w) of polyethylene glycol (PEG) polymers, about 4% w/w of tyloxapol and about 66% (w/w) of nepafenac, wherein the formulation is adapted to release the nepafenac at therapeutically effective levels each day for a period of about two weeks to about four weeks.

9. The drug insert of claim 1, wherein the solid matrix is configured as a medical device.

10. The drug insert of claim 9, wherein the medical device has a substantially cylindrical shape.

11. The drug insert of claim 9, wherein the medical device is configured for deposition within or adjacent to an eye.

12. The drug insert of claim 9, wherein the medical device is configured for deposition within a lacrimal canaliculus.

13. The drug insert of claim 9, further comprising a sheath body disposed at least partially over the solid matrix.

14. The drug insert of claim 1, wherein the solid matrix does not comprise methacrylate polymers and methacrylate monomers.

15. The drug insert of claim 1, comprising about 204 mg of nepafenac or less.

16. A drug insert for topical delivery of nepafenac, comprising about 20% (w/w) of polycaprolactone, about 10% (w/w) of polyethylene glycol (PEG) polymers, about 4% w/w of tyloxapol and about 66% (w/w) of nepafenac.

17. The drug insert of claim 16, wherein the formulation is adapted to release the nepafenac at therapeutically effective levels each day for a period of about two weeks to about four weeks.

18. The drug insert of claim 16, further comprising a sheath body disposed at least partially over the solid matrix.

19. The drug insert of claim 1, configured for deposition within a lacrimal implant.

20. The drug insert of claim 19, adapted to release the nepafenac at therapeutically effective levels each day for a period of about two weeks to about four weeks for treatment of pain.

* * * * *